(12) United States Patent  (10) Patent No.: US 7,678,141 B2
Greenan et al.  (45) Date of Patent: Mar. 16, 2010

(54) STENT GRAFT HAVING A FLEXIBLE, ARTICULABLE, AND AXIALLY COMPRESSIBLE BRANCH GRAFT

(75) Inventors: Trevor Greenan, Santa Rosa, CA (US); James Machek, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 233 days.

(21) Appl. No.: 11/379,112

(22) Filed: Apr. 18, 2006

(65) Prior Publication Data

US 2007/0244542 A1 Oct. 18, 2007

(51) Int. Cl.
*A61F 2/06* (2006.01)
(52) U.S. Cl. .................. 623/1.13; 623/1.35
(58) Field of Classification Search ........... 623/1.13, 623/1.35, 1.28, 1.29, 1.3, 1.31; *A61F 2/06*
See application file for complete search history.

(56) References Cited

U.S. PATENT DOCUMENTS

| 5,984,955 | A |   | 11/1999 | Wisselink |   |
|---|---|---|---|---|---|
| 6,053,938 | A | * | 4/2000 | Goldmann et al. | 623/1.15 |
| 6,270,524 | B1 |   | 8/2001 | Kim |   |
| 6,283,991 | B1 | * | 9/2001 | Cox et al. | 623/1.13 |
| 6,350,248 | B1 |   | 2/2002 | Knudson et al. |   |
| 6,428,565 | B1 |   | 8/2002 | Wisselink |   |
| 2004/0193254 | A1 |   | 9/2004 | Greenberg et al. |   |
| 2005/0113905 | A1 | * | 5/2005 | Greenberg et al. | 623/1.16 |
| 2005/0131517 | A1 |   | 6/2005 | Hartley et al. |   |
| 2005/0267566 | A1 | * | 12/2005 | Rioux et al. | 623/1.28 |
| 2006/0155359 | A1 | * | 7/2006 | Watson | 623/1.13 |
| 2007/0179592 | A1 | * | 8/2007 | Schaeffer | 623/1.35 |
| 2007/0244547 | A1 | * | 10/2007 | Greenan | 623/1.35 |

FOREIGN PATENT DOCUMENTS

| EP | 0699423 | 3/1996 |
| WO | WO97/27898 | 8/1997 |
| WO | WO2004/064686 | 4/2004 |
| WO | WO2005/046526 | 5/2005 |

* cited by examiner

*Primary Examiner*—Corrine M McDermott
*Assistant Examiner*—Jason-Dennis Stewart
(74) *Attorney, Agent, or Firm*—Serge Hodgson

(57) ABSTRACT

A stent graft and method for positioning and deploying the stent graft within a vessel system that includes a main vessel and a branch vessel emanating from the main vessel. The stent graft includes a tubular shaped main body formed from graft material, a branch opening (aperture)(ring) in the graft material of the main body whose position can be varied. A tubular shaped branch graft can extend from the main graft. A side wall of the main body may be configured as a series of connected annular corrugations or pleats, and coupled to the main body to define and provide variable positioning of its branch opening (aperture).

8 Claims, 20 Drawing Sheets

STENT GRAFT HAVING A FLEXIBLE, ARTICULABLE, AND AXIALLY COMPRESSIBLE BRANCH GRAFT

BACKGROUND OF THE INVENTION

1. Field of the Invention

The present invention relates to endoluminal stent graft structures. More particularly, the present invention relates to endoluminal stent grafts for use in a body vessel system that includes a main vessel and a branch vessel emanating from the main vessel.

2. Description of Related Art

A conventional endoluminal stent graft typically includes a radially expandable reinforcement structure, formed from a plurality of annular stent rings, and a cylindrically shaped graft material defining a main body to which the stent rings are coupled. Stent grafts are well known for use in tubular shaped human vascular or other body vessel.

At deployment, after intravascular insertion and transluminal transport, i.e., within the vessel, to the point of use within a damaged or diseased vessel, for example, an aneurysmal artery, a compressed stent graft is radially expanded. A stent graft is self-expandable or expandable by application of pressure applied outwardly to the interior portion of the stent graft. After deployment, the stent graft is fixed in place at the location of initial deployment within the vessel. Complications such as Type I endoleaks can occur if the stent graft migrates after deployment.

One approach in the prior art, used to securely fix the stent graft to the vessel at the point of initial deployment, relied on providing the stent graft with an outward biasing radial force at the contact interface between the stent graft and the interior wall of the vessel in which it was deployed. Typically, a radial force, biasing outwardly from the stent graft toward the interior wall of the vessel, was supplied by a spring element at one or both ends of the stent graft. The spring element urged the stent graft into abutting contact with the interior wall of the vessel where frictional forces between the spring element and the vessel interior wall provided both a liquid-tight seal between the stent graft and the vessel as well as fixation of the stent graft at its location of initial deployment.

In cases where the contact interface, sometimes called the landing zone, between the stent graft and the vessel wall is small, the surface area on the interior of the vessel available for application of outward radial force may be insufficient to firmly and permanently seal and fix the stent graft. An abdominal aortic aneurysm with a short "neck" for a landing zone is an example where the area available for application of radial force might not be enough to seal and fix a stent graft.

Accordingly, in the prior art, stent grafts sometimes included bare springs to extend the length of the stent graft such that the spring element contacted and could be fixed to healthy vessel tissue above or below the area of weakened or damaged vessel tissue.

Illustratively, FIG. 1A shows a partial cutaway view of a vessel system 150, for example an artery system, containing one example of a deployed prior art stent graft 100. Vessel system 150 includes a main vessel 152, for example an aorta, and one or more branch vessels 154 emanating from main vessel 152, such as renal arteries emanating from the aorta. Main vessel 152 includes an aneurysm 156, i.e., a weakened, radially distending vessel segment, caused by disease. Aneurysm 156 is at risk of rupture resulting in, for example, extravasation of blood into the peritoneal cavity or into tissue surrounding diseased main vessel 152.

An evolving method for treating aneurysmal disease of the type depicted in FIG. 1A, is termed "endovascular aneurysmal exclusion". The goal of endovascular aneurysmal exclusion is to exclude from the interior of aneurysm 156, i.e., an aneurysmal sac 158, all aorta pressurized fluid flow, thereby reducing the risk of rupture of aneurysm 156 requiring invasive surgical intervention.

One procedure developed to accomplish this goal entailed internally spanning affected main vessel 152 with stent graft 100. Prior art stent graft 100 was positioned and deployed within main vessel 152 through a vessel system furcation 159, such as an iliac artery of an artery system, with an insertion stent graft catheter (not shown) by percutaneous or cut-down procedures well know to those of skill in the art. Prior art stent graft 100 typically included a radially expandable cylindrical reinforcement structure, sometimes referred to simply as a stent 104, formed from a plurality of annular stent rings 106 coupled to a biocompatible tubular graft material 102. A bare spring element 108 of prior art stent graft 100 was coupled to the proximal end of stent graft material 102.

Graft material 102 was configured in a tubular shape forming a main body 103 spanning across aneurysm 156. Prior art stent graft 100 was fixed in main vessel 152 by bare spring element 108 which helped established a substantially fluid-tight seal above aneurysm 156 at a graft/vessel interface, sometimes called a landing zone 160. Once deployed, prior art stent graft 100 provided an alternate conduit for fluid flow through main body 103 and, at the same time, excluded fluid flow into aneurysmal sac 158.

In the prior art stent graft 100 of FIG. 1A, graft material 102 did not extend beyond a branch point 162, where branch vessel 154 begins to emanate from main vessel 152, to the end of prior art stent graft 100 at bare spring element 108. If graft material 102 were extended such that it passed by a vessel ostium 166 leading into branch vessel 154 from main vessel 152, graft material 102 would block vessel ostium 166 and cut-off fluid flow into branch vessel 154.

However, graft material 102 forming main body 103 may be advantageously utilized to assist in forming a liquid-tight seal between prior art stent graft 100 and healthy tissue beyond branch point 162 at landing zone 160 at the interior wall of main vessel 152 above diseased or damaged tissue at a neck 164 of aneurysm 156. FIG. 1B shows a close-up, cross-section view of one branch point 162 of vessel system 150 of an embodiment similar to that shown in FIG. 1A containing an example of a deployed prior art stent graft 180 that further includes extended graft material 102E beyond branch point 162.

In FIG. 1B, to address the problem of blocking of vessel ostium 166, extended graft material 102E included a branch opening (aperture) 110. Thus, prior art custom configured stent graft 180 with a side window or fenestration was often referred to as a "fenestrated" stent graft. At deployment, prior art stent graft 180 was main axially and rotationally positioned within main vessel 152 such that branch opening (aperture) 110 aligned with vessel ostium 166 when prior art stent graft 180 was radially expanded. In this configuration, a portion of the fluid flow proceeded from main vessel 152, through branch opening (aperture) 110, through vessel ostium 166, and into branch vessel 154.

It is well known by those of skill in the art that a vessel system 150 is by nature tortuous, asymmetrical and, within limits, individually variable. Thus, when deploying prior art stent graft 180 it was often difficult to position branch opening (aperture) 110, both main axially along main vessel 152 and rotationally about main vessel 152, exactly at vessel ostium 166. Misalignment between branch opening (aperture) 110 in extended graft material 102E and vessel ostium 166 could result in partial or complete blocking of vessel ostium 166 thereby restricting or completely cutting-off fluid flow into branch vessel 154, which is unacceptable. Even when (ring) branch opening (aperture) 110 was substantially aligned with vessel ostium 166 at initial deployment, slight migration of prior art stent graft 180 could cause subsequent misalignment and resultant fluid flow blockage.

However, a rigid ring branch opening (aperture) 110 was branch axially centered along a branch graft central axis $L_b$ that is substantially perpendicular to a main body central axis $L_m$ of main body 152. As noted above, stent grafts were generally compressed in a radial and not axial direction prior to deployment. Also, the axial and rotational alignment difficulties described above continue to be an issue.

Further, branch vessel 154 is often not completely perpendicular to main vessel 152. The branch angle between branch vessel 154 and main vessel 152 often varies from patient to patient given the tortuous and asymmetrical nature of vessels. Accordingly, prior art stent graft 180 containing a rigid (ring) branch opening (aperture) 110 was often custom fabricated, at considerable expense, to accommodate the vessel structure of a particular patient and to attempt to avoid misalignment.

What is needed is a stent graft containing a branch opening (aperture) or graft that is simply configurable into a compressed state prior to deployment. Further, what is needed is a branch opening (aperture) or graft that is easily aligned with, and conforms, without kinking or collapsing, to a tortuous and asymmetrical branch vessel in which it is deployed.

SUMMARY OF THE INVENTION

Examples according to the present invention provide an innovative device and method for compressing and aligning a branch graft that conforms to a tortuous, asymmetrical branch vessel, emanating from a main vessel, to provide support to, and a conduit for fluid flow into the branch vessel.

In one example, a stent graft includes a main body having a main body side wall, a branch opening (aperture) formed in the main body, and at least one branch graft having a branch graft side wall formed from a series of connected corrugations or pleats, and coupled to the main body at its branch opening (aperture). The branch graft is in fluid communication with the main body such that, together, they provide a conduit for fluid flow from a main vessel into a branch vessel emanating from the main vessel. Further, the series of connected pleats of graft material forming the branch graft side wall of the branch graft provide flexible, articulable, and axial compressible properties to the branch graft.

In one example, the main body side wall of the main body is formed from a graft material configured in a tubular shape and defining the branch opening (aperture) in the main body side wall. The branch graft is also formed from a graft material configured in a tubular shape with the branch graft side wall formed as connected annular shaped pleats. In other examples, the stent graft further includes annular shaped stent rings and bare spring elements coupled to the graft material of the main body and/or the branch graft.

In use, the stent graft, in a compressed configuration, is inserted into and transluminally advanced along the main vessel, for example, an aorta. Utilizing endovascular procedures and vascular imaging techniques well know to those of skill in the art, the stent graft is positioned such that the branch opening (aperture) or graft is substantially aligned, both along the main axis and rotationally within the flexible and articulable range of the branch opening (aperture) or graft, with a vessel ostium in the main vessel leading into the branch vessel. The main axial and rotational position of the branch opening (aperture) or graft is determined before deployment of the main body of the stent graft and adjusted, if necessary, to more closely position the branch opening (aperture) or graft with respect to the vessel ostium leading into the branch vessel. The main body is then radially expanded within the main vessel. Finally, the branch graft is branch axially (or laterally) expanded into the branch vessel.

For clarity of presentation, embodiments according to the present invention are described below in terms of a stent graft within the aorta at the intersection of a branch to the renal arteries.

DETAILED DESCRIPTION

Figure 2:
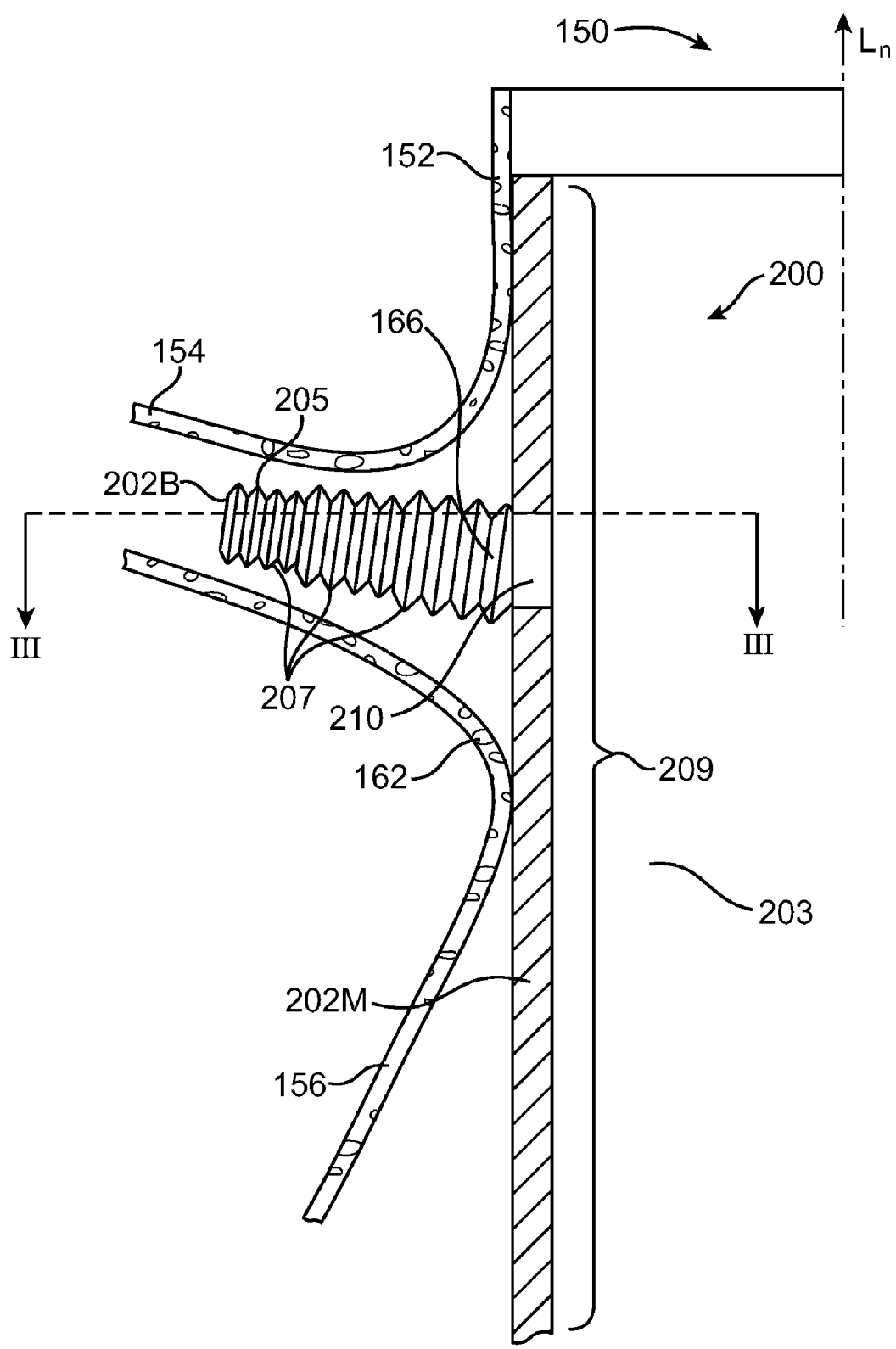
FIG. 2 shows a close-up partial cutaway view of the vessel system containing a stent graft, positioned and deployed for use, that includes an example of a branch opening (aperture) and graft.
Figure 3:
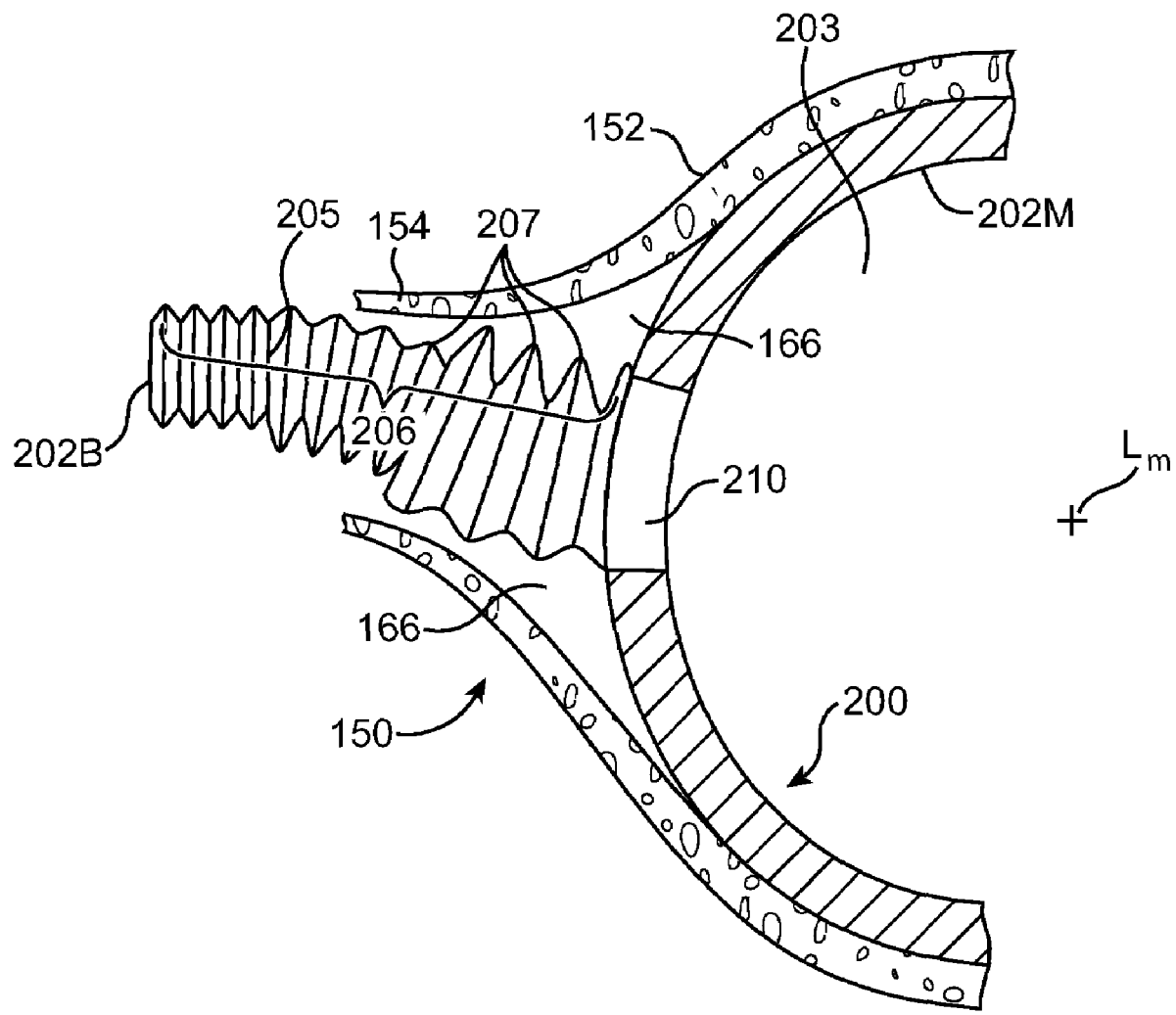
FIG. 3 shows a cross sectional top view of the stent graft shown in FIG. 2 taken along line III-III.

FIG. 2 shows a close-up partial cutaway view of vessel system 150 containing a stent graft 200, positioned and deployed for use, that includes an example of a branch graft 205. FIG. 3 shows a cross sectional view of the stent graft of FIG. 2 taken along line III-III. For clarity of presentation, in FIGS. 2 and 3 the previously described stent reinforcing structures and bare spring elements are not shown, although it should be understood that the present embodiment may include some or all of these structures in certain examples.

Referring to FIGS. 2 and 3 together, a main graft material 202M is configured in a tubular shape defining a main body 203 having a main body side wall 209 spanning aneurysm 156 (FIG. 2) affecting main vessel 152. Vessel system 150 includes branch vessel 154, for example, a renal artery, emanating from main vessel 152 at a branch point 162 (lower edge of ostium) (FIG. 2). Main vessel 152 includes a vessel ostium 166 in main vessel 152 leading into branch vessel 154.

Deployed in branch vessel 154, is a tubular shaped branch graft 205 having a branch graft side wall 206 (FIG. 3) of at least one series of connected pleats 207 formed from biocompatible branch graft material 202B. Main graft material 202M defines a branch opening (aperture) 210 in main body 203 or, more particularly, in main body side wall 209. Branch graft 205 is coupled to main body 203 at branch opening (aperture) 210 such that branch graft 205 is in fluid communication with main body 203.

As described more fully below with reference to FIGS. 5A-5E, branch graft side wall 206 formed of connected annularly shaped pleats 207 makes branch graft 205 flexible and articulable in the manner of a bellows. Said by way of simile, branch graft side wall 206, formed of connected pleats 207, provides branch graft 205 with the flexible and articulable characteristics of an "elephant trunk". The particular properties of branch graft side wall 206 allow stent graft 200 to accommodate a relatively large degree of misalignment between branch graft opening 210 and vessel ostium 166 in main body 203 prior to deployment. Additionally, flexible and articulable branch graft 205 easily conforms, without kinking or collapsing, to the tortuous nature of branch vessel 154 after deployment.

Further, as also described more fully below with reference to FIG. 5F, branch graft 205 along with branch graft side wall 206 formed of connected pleats 207, are also compressible branch axially along a branch graft central axis, likewise in the manner of a bellows.

Figure 4A:
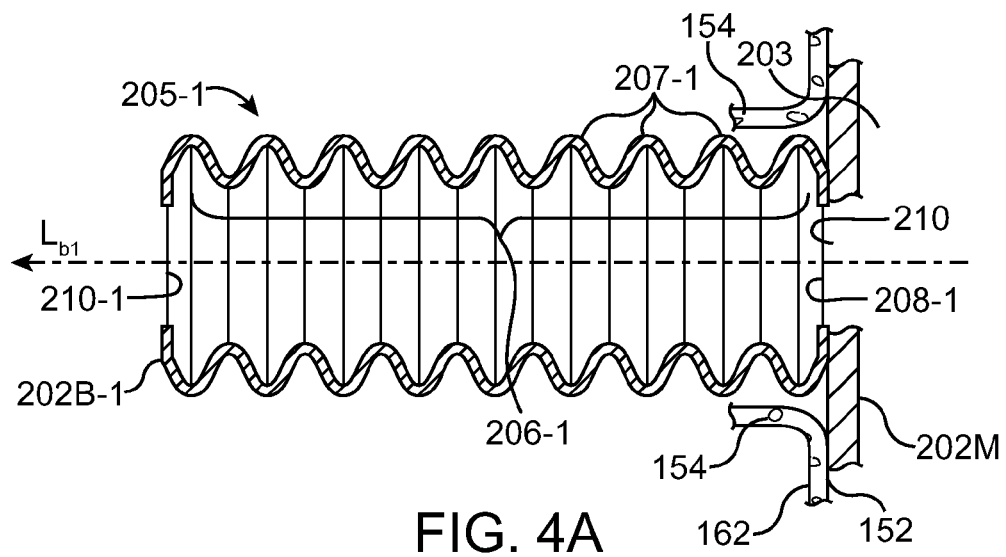
FIG. 4A shows a cross-sectional view taken perpendicular to the branch axis of one example of a branch graft.
Figure 4B:
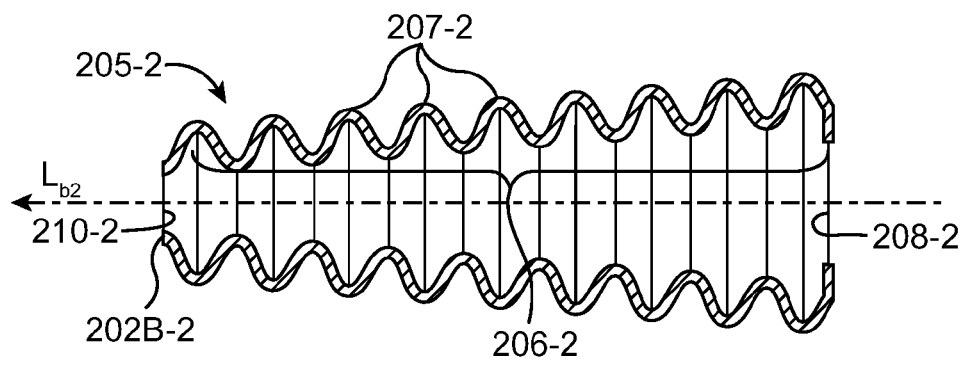
FIG. 4B shows a cross-sectional view taken perpendicular to the central axis of another example of a branch graft.
Figure 4C:
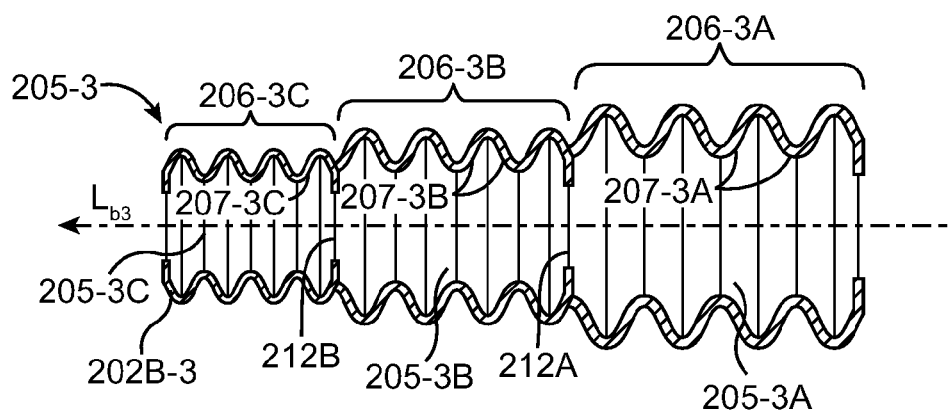
FIG. 4C shows a cross-sectional view taken perpendicular to the central axis of yet another example of a branch graft.

More particularly, FIGS. 4A, 4B, and 4C are cross-sectional views taken perpendicular to respective main branch graft central axes $L_{b1}$, $L_{b2}$, and $L_{b3}$, of three example branch grafts 205-1, 205-2, and 205-3. In FIG. 4A, branch graft 205-1 is formed as a single-piece, hollow, generally cylindrically shaped tube fabricated from branch graft material 202B-1. A branch graft side wall 206-1 of branch graft 205-1 is made up of a single series of uniform, connected, annularly shaped pleats 207-1. Branch graft 205-1 further defines a fluid inlet 208-1 at a first end of branch graft 205-1 and a fluid outlet 210-1 at a second opposite end of branch graft 205-1. Fluid inlet 208-1 provides for fluid flow into branch graft 205-1 and fluid outlet 210-1 provides for fluid flow out from branch graft 205-1.

Branch graft 205-1 is coupled to main body 203 such that fluid inlet 208-1 aligns with branch opening (aperture) 210. In use, branch graft is deployed within branch vessel 154 with fluid outlet (opening) 210-1 placed within the outer perimeter of the vessel ostium 166. In this configuration, branch graft 205-1 is in fluid communication with branch opening (aperture) 210 and thus main body 203. A portion of fluid flowing through main vessel 152 into main body 203 is directed into branch graft 205-1, through branch opening (aperture) 210, through branch graft inlet 208-1, exiting through branch graft outlet 210-1 into branch vessel 154.

In another example, in FIG. 4B, branch graft 205-2 is formed as a hollow, generally tapered shaped tube fabricated from branch graft material 202B-2. The frusto-conical surface shaped branch graft side wall 206-2 of branch graft 205-2 is made up of one series of connected annularly shaped pleats 207-2 of diminishing diameter from fluid inlet 208-2 at a first end of branch graft 205-2 to fluid outlet 210-2 at a second opposite end of branch graft 205-2. Branch graft 205-2 is coupled to main body 203 and provides fluid flow from main vessel 152 similarly to those described above with reference to branch graft 205-1, and so are not shown nor described further.

In another example, in FIG. 4C, branch graft 205-3 is formed as a first, a second, and a third hollow, generally cylindrically shaped tube 205-3A, 205-3B and 205-3C, respectively, fabricated from branch graft material 202B-3. A branch graft side wall first portion 206-3A of first tube 205-3A, made up of a series of connected uniform annularly shaped first pleats 207-3A, is coupled to a branch graft side wall second portion 206-3B of second tube 205-3B, made up of a series of connected uniform annularly shaped second pleats 207-3B. The diameter of second pleats 207-3B is less than the diameter of first pleats 207-3A. Branch graft side wall second portion 206-3B of second tube 205-3B is, in turn, coupled to a branch graft side wall third portion 206-3C of third tube 205-3C, made up of a series of connected uniform annularly shaped third pleats 207-3C. The diameter of third pleats 207-3C is less than the diameter of second pleats 207-3B.

Branch graft 205-3 is coupled to main body 203 in a manner similar to that described above with reference to branch graft 205-1 and so is not shown nor described further. Further, branch graft 205-3 provides fluid flow from main body 203 in manner similar to that described above with additionally, a first intermediate port 212A, at the coupling of branch graft side wall first portion 206-3A and branch graft side wall second portion 206-3B, providing fluid flow from first tube 205-3A into second tube 205-3B, and a second intermediate port 212B, at the coupling of branch graft side wall second portion 206-3B and branch graft side wall third portion 206-3C, providing fluid flow from second tube 205-3B into third tube 205-3C.

The flexible, articulable, bellows-like structures of branch grafts 205-1, 205-2, and 205-3 accommodate a relatively large degree of main axis and rotational (angular) misalignment between a main graft (e.g., 203) and respective vessel ostia 166 (FIGS. 2 and 3) in main vessel 152 prior to deployment. Additionally, flexible and articulable branch grafts 205-A, 205-B, and 205-C easily conform, without kinking or collapsing, to the tortuous nature of their respective branch vessel 154 after deployment.

Figure 5A:
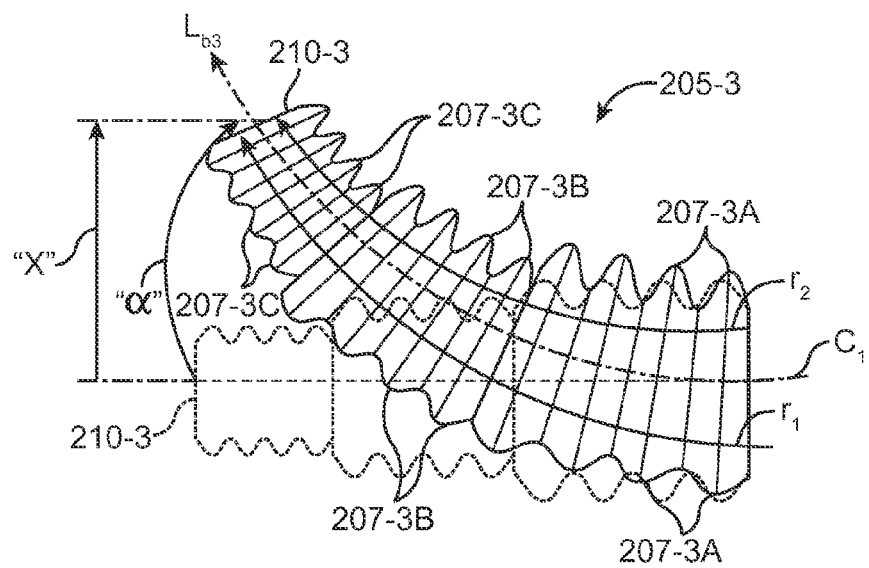
FIG. 5A shows a side view of the example branch graft of FIG. 4C depicting its flexible and articulable properties in the single plane of the drawing.
Figure 5B:
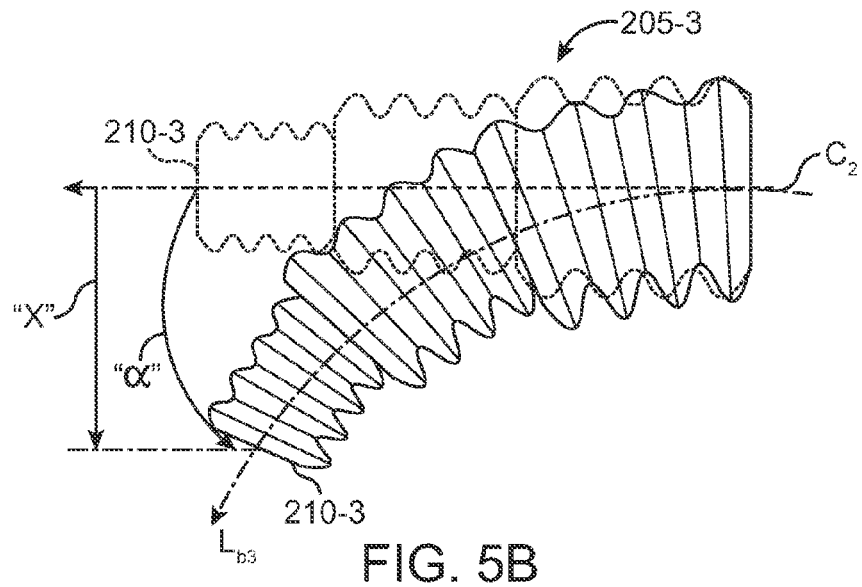
FIG. 5B shows a side view of the example branch graft of FIG. 4C further depicting its flexible and articulable properties in the single plane of the drawing.
Figure 5C:
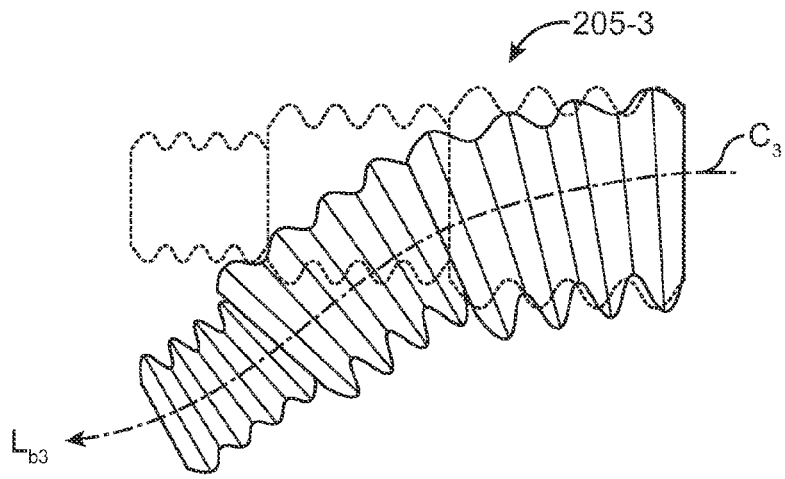
FIG. 5C shows a side view of the example branch graft of FIG. 4C yet further depicting its flexible and articulable properties in the single plane of the drawing.

Illustratively, FIGS. 5A, 5B, and 5C are side views depicting the flexible and articulable properties of example branch graft 205-3 of FIG. 4C in the single plane of the drawings. In one example shown in FIG. 5A, branch graft 205-3 flexibly bends upward configuring branch graft central axis $L_{b3}$ in a curve C1. In this upwardly bent configuration, the portion of first pleats 207-3A, second pleats 207-3B, and third pleats 207-3C at the top of branch graft 205-3, partially compress and fold-in one upon the other, allowing the top of branch graft 205-3 to form an inside radius r2 to curve C1. At the same time, the portion of first pleats 207-3A, second pleats 207-3B, and third pleats 207-3C at the bottom of branch graft 205-3, expand and stretch apart one from the other, allowing the bottom of branch graft 205-3 to form to form an inside radius r1 to curve C1. Thus as shown, radius r2 is less than radius r1, allowing branch graft 205-3 to bend and articulate upwardly. In this configuration, fluid outlet 210-3 is displaced upwardly by a displacement distance "X" and angled clockwise by a rotation angle "α" relative to the unbent configuration of branch graft 205-3, indicated in dotted outline.

In one example shown in FIG. 5B, branch graft 205-3 flexibly bends downward in mirror image to FIG. 5A with fluid outlet 210-3 displaced downwardly by a displacement distance "-X" and is angled counter-clockwise by a rotation angle "-α" relative to the unbent configuration of branch graft 205-3, indicated in dotted outline.

In another example shown in FIG. 5C branch graft 205-3 defines a compound curve C3 along branch graft central axis $L_{b3}$, bending first in downward direction and then in an upward direction.

Figure 5D:
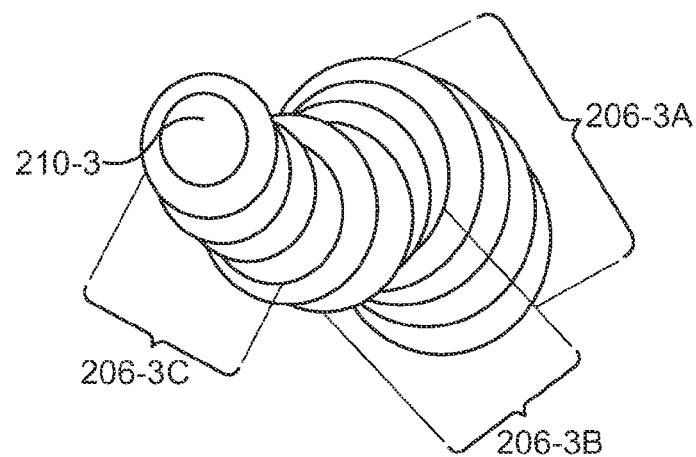
FIG. 5D shows a perspective view of FIG. 5C.

FIG. 5D shows a perspective view of branch graft 205-3 configured as in FIG. 5C. As shown in FIGS. 5C and 5D, branch graft side wall second portion 206-3B bends downward relative to branch graft side wall first portion 206-3A and branch graft side wall third portion 206-3C bends upward relative to branch graft side wall second portion 206-3B.

Figure 5E:
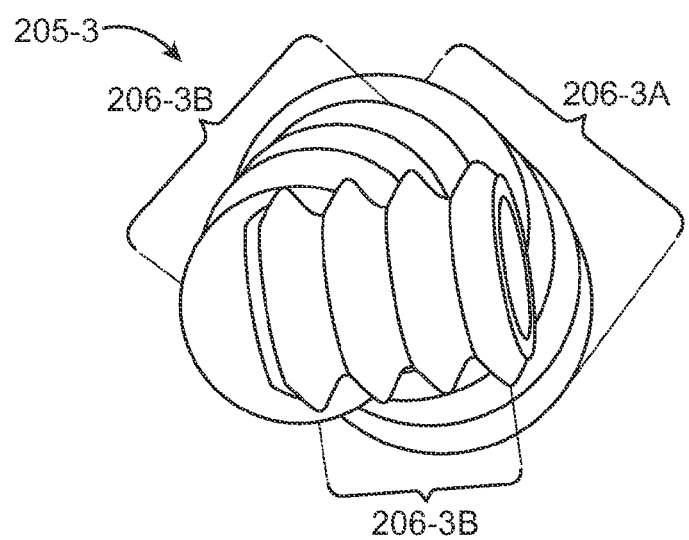
FIG. 5E shows a perspective view depicting the flexible and articulable properties in more than one plane of the example branch graft of FIG. 4C.
Figure 5F:
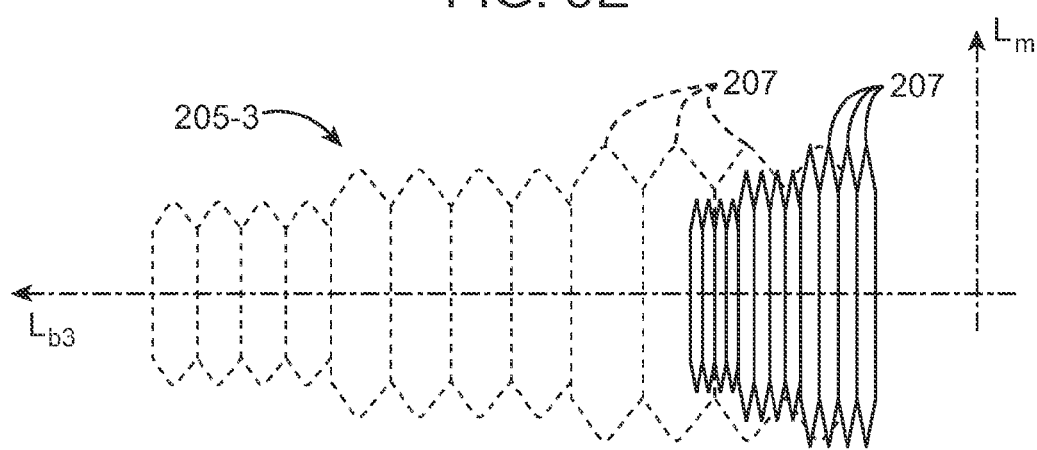
FIG. 5F shows a side view of the example branch graft of FIG. 4C in a compressed configuration.

Further, as may be readily observed by referring to orthogonally juxtaposed FIGS. 2 and 3 together, in one example, the bending and articulation of branch grafts is not restricted to a single plane. Illustratively, FIG. 5E is a perspective view depicting the flexible and articulable properties in more than one plane of branch graft 205-3 of FIG. 4C. As shown, branch graft 205-3 defines a complex curve where branch graft side wall second portion 206-3B bends downward relative to branch graft side wall first portion 206-3A and branch wall side wall third portion 206-3C bends laterally out of the plane defined by branch graft side wall first portion 206-3A and branch graft side wall second portion 206-3B.

Thus, the flexible, articulable, bellows-like structures of the branch graft examples described above are designed to accommodate a relatively large degree of main axial and rotational (angular) misalignment between branch graft openings and respective vessel ostia in main vessels prior to deployment. The fluid outlets of the various branch grafts may be easily flexed and articulated to accommodate a relatively large amount of misalignment with vessel ostia leading to branch vessels in which the branch grafts is deployed. Additionally, flexible and articulable branch grafts easily conform, without kinking or collapsing, to the tortuous nature of their respective branch vessels after deployment.

Finally, as noted briefly above, the examples of branch grafts above are also branch axially compressible. Illustratively, FIG. 5F shows a side view of the example branch graft 205-3 of FIG. 4C in a compressed configuration. Relative to an expanded configuration depicted in dotted outline, connected pleats 207 easily fold-in and overlie one upon the other, bellows-like, when branch graft 205-3 is compressed branch axially along branch graft central axis $L_{b3}$, in a direction approximately perpendicular to main body central axis $L_m$. As can be readily appreciated, example branch graft 205-1 of FIG. 4A and example branch graft 205-2 of FIG. 4B are likewise easily configurable into a compressed state along their respective branch graft central axes $L_{b1}$ and $L_{b2}$.

Figure 5G:
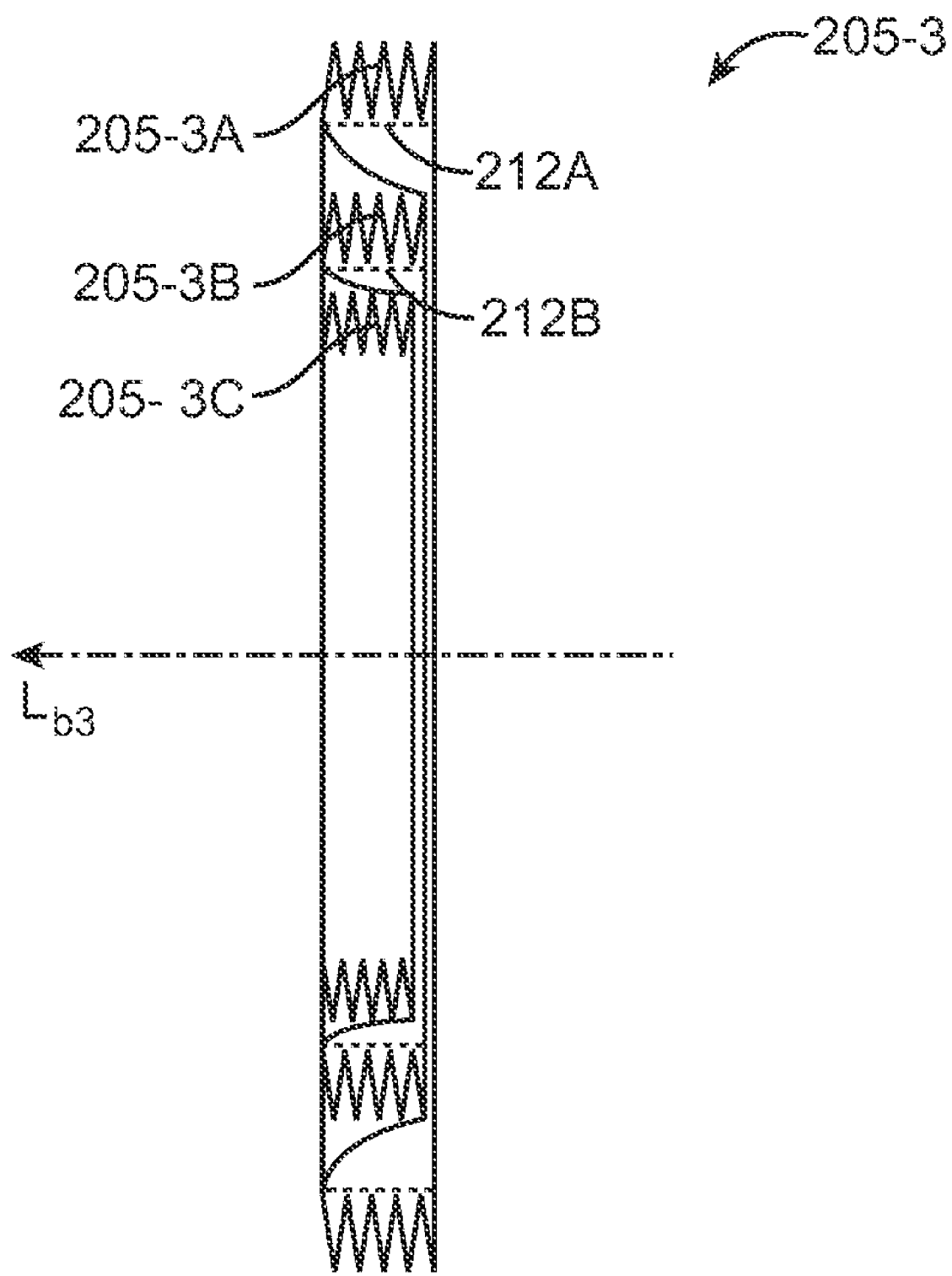
FIG. 5G shows a cross sectional view of the example branch graft of FIG. 4C in a compressed configuration taken along its central axis.

Further, FIG. 5G shows a cross sectional view of example branch graft 205-3 of FIG. 4C taken along branch graft central axis $L_{b3}$ with first, second, and third tubes 205-3A, 205-3B, and 205-3C, respectively, telescoped into one another. Referring to FIGS. 4C and 5G together, when compressed into the configuration shown in FIG. 5G, third tube 205-3C of example branch graft 205-3 telescopes through second intermediate port 212B and nests within second tube 205-3B, which, as a unit, likewise telescopes through first intermediate port 212A and nests within first tube 205-3A of branch graft 205-3. Advantageously, in this highly compressed nested configuration, branch graft 205-3 presents a very thin side profile when coupled to main graft material 202M of main body 203 (FIG. 4A).

Figure 7:
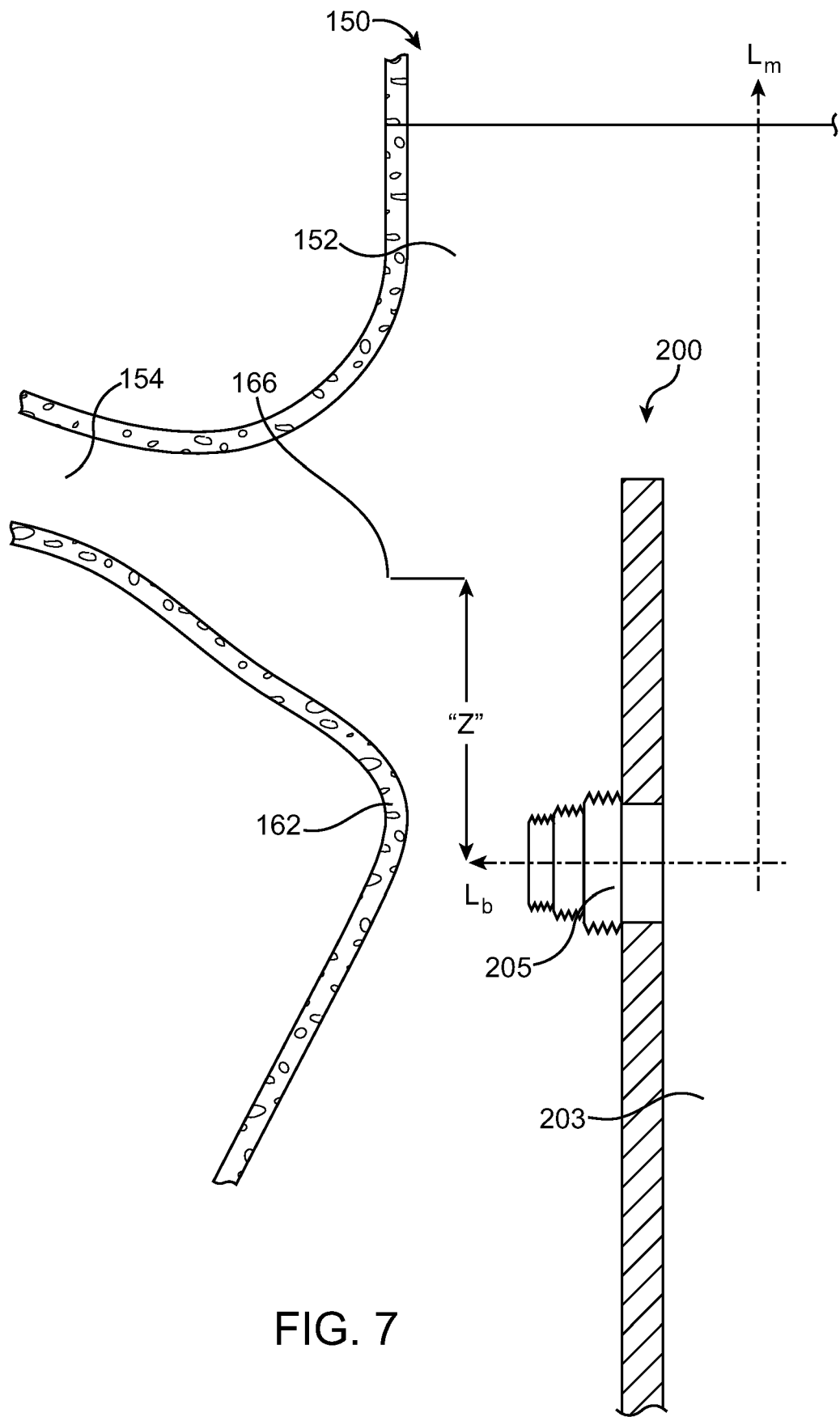
FIG. 7 shows a close-up partial cutaway view of a vessel system containing an example of a stent graft in a compressed configuration and positioned along a main vessel such that a branch stent graft branch opening (aperture) is main axially misaligned below a branch point of the vessel system.

Thus, as described above, flexible, articulable, and branch axially compressible branch graft 205 is formed from at least one series of connected annular pleats 207, and is coupled to and in fluid communication with main body 203 at branch opening (aperture) 210. Further, as shown in FIG. 7 and as described more fully below, prior to deployment, stent graft 200 in its entirety, including main body 203 and branch graft 205, is easily configurable into a compressed state. Main body 203 is compressible radially in directions inward and perpendicular with respect to main body central axis $L_m$. At the same time, branch graft 205 is compressible branch axially in a direction along branch graft central axes $L_b$, also in a direction perpendicular with respect to a main body central axis $L_m$, i.e., also in a direction of radial compression of main body 203. Main body 203 is compressible radially and branch graft 205 is compressible branch axially by application of forces directed perpendicular toward main body central axis $L_m$.

Figure 6A:
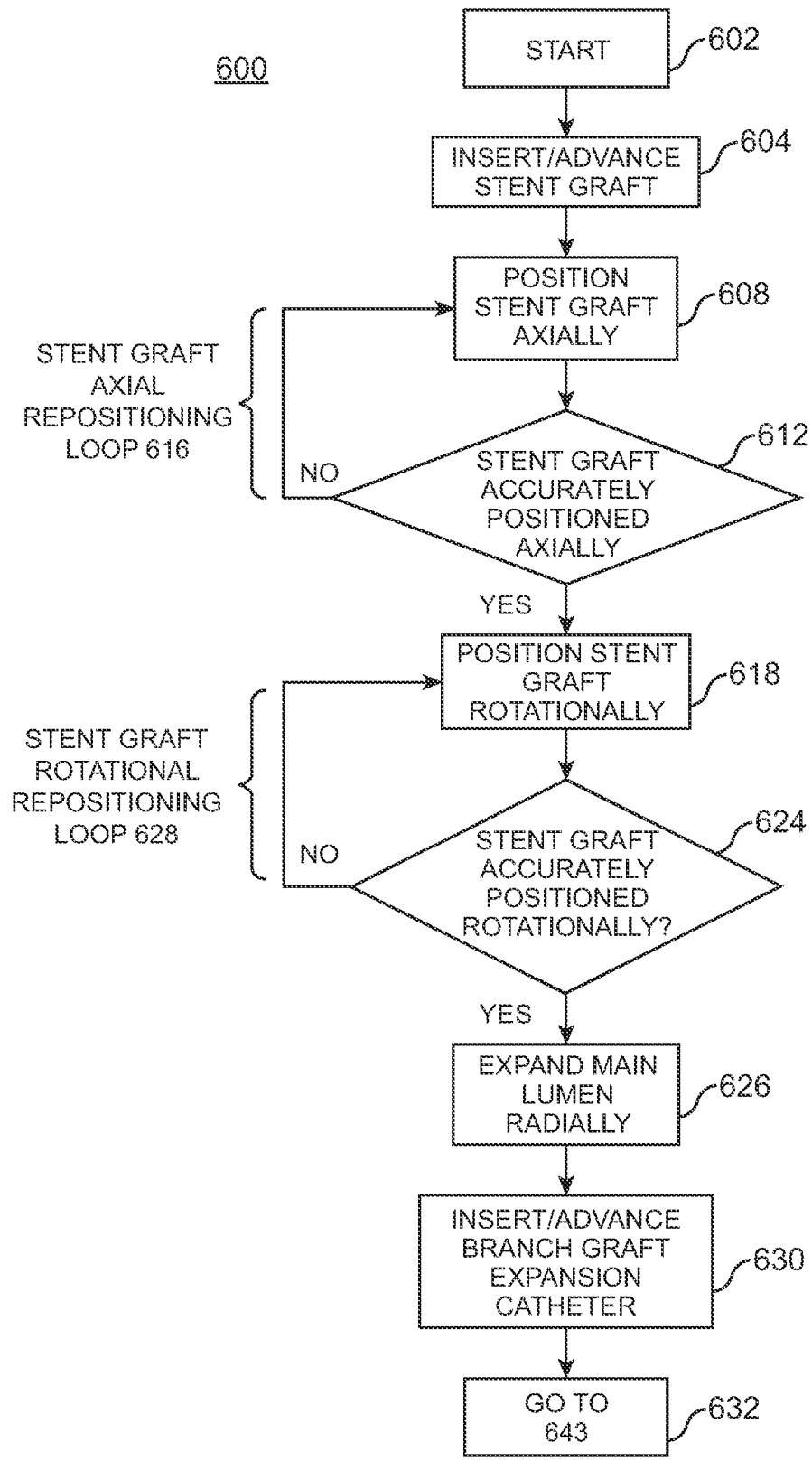
FIG. 6 is a key to FIGS. 6A and 6B, which show an example process flow diagram for a method of using the stent graft.
Figure 6B:
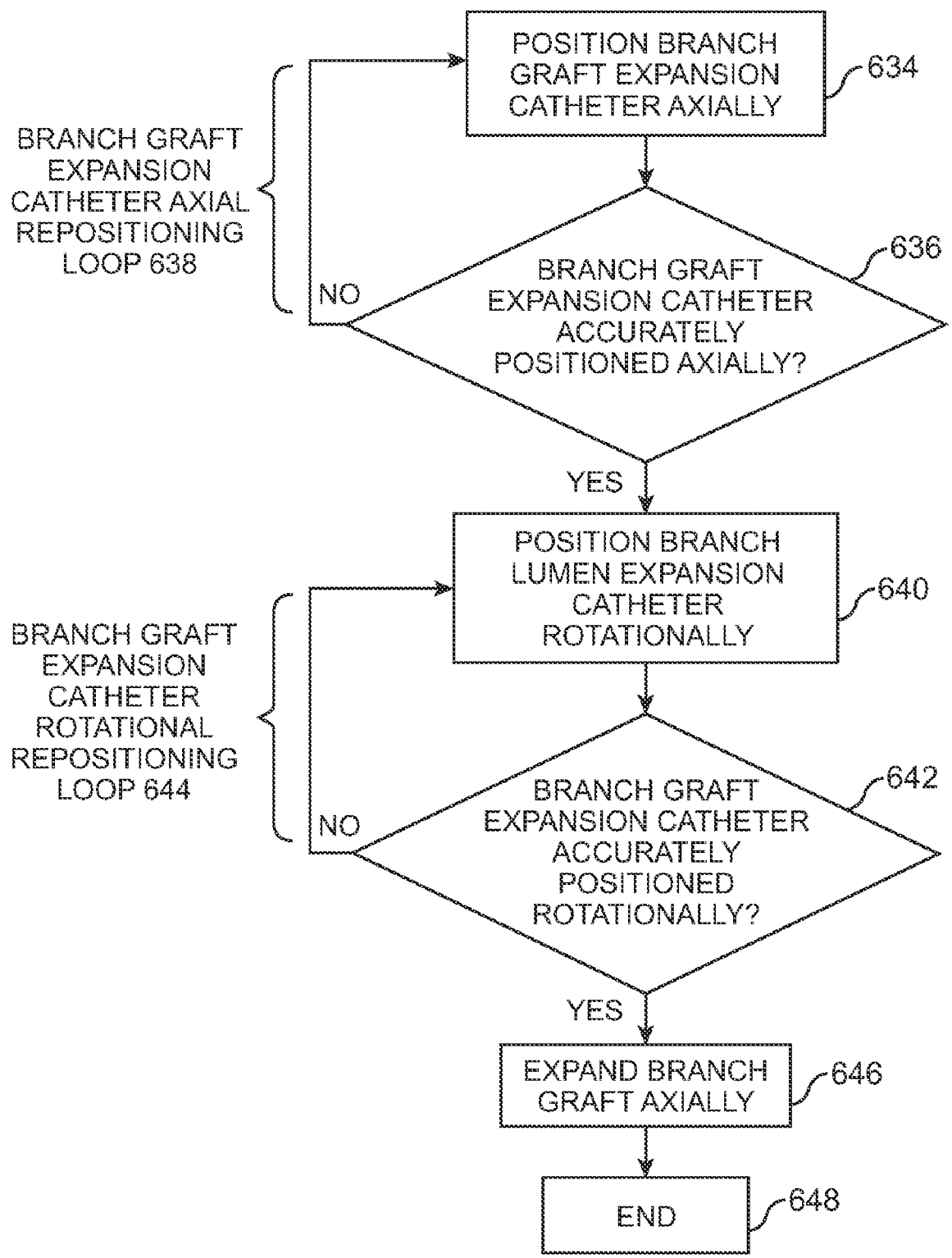

A method of use of the stent graft is next described. FIG. 6 is a key to FIGS. 6A and 6B, which show a process flow diagram for a Method 600 of using stent graft 200 of FIGS. 2 and 3. FIG. 7 shows a close-up partial cutaway view of vessel system 150 containing stent graft 200 in a compressed configuration and positioned along main vessel 152 such that the initial opening of branch graft 205 is main axially misaligned and located below branch point 162 of vessel system 150. Referring to FIGS. 6 and 7 together, Start Operation 602 of Method 600 commences use of stent graft 200 containing flexible articulable branch graft 205. Start Operation 602 transfers to Insert/Advance Stent Graft Operation 604. When it is stated herein that a first operation transfers to a second operation, those of skill in the art understand that the first operation is completed and the second operation is started.

Figure 1A:
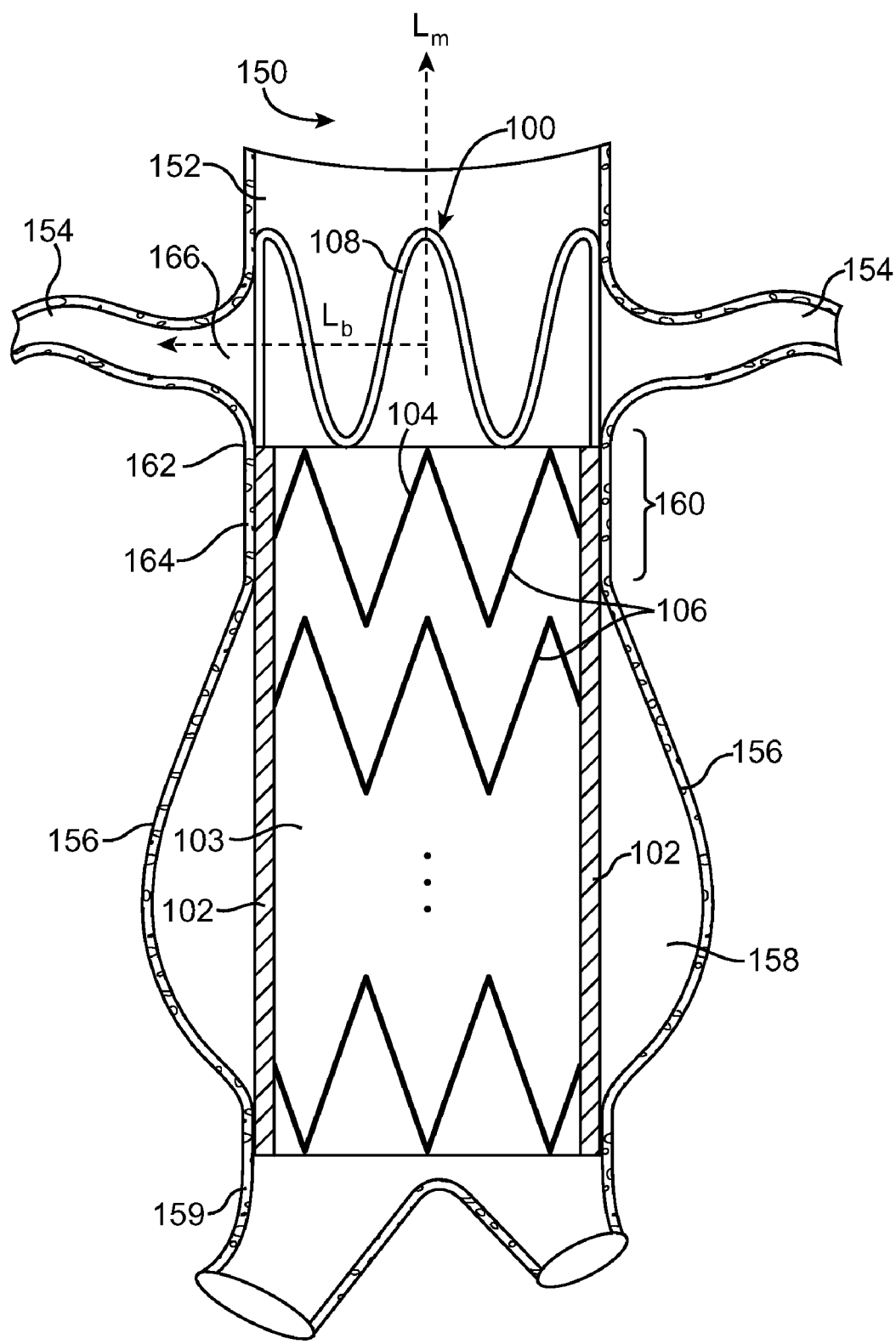
FIG. 1A shows a partial cutaway view of a vessel system containing one example of a deployed prior art stent graft.
Figure 1B:
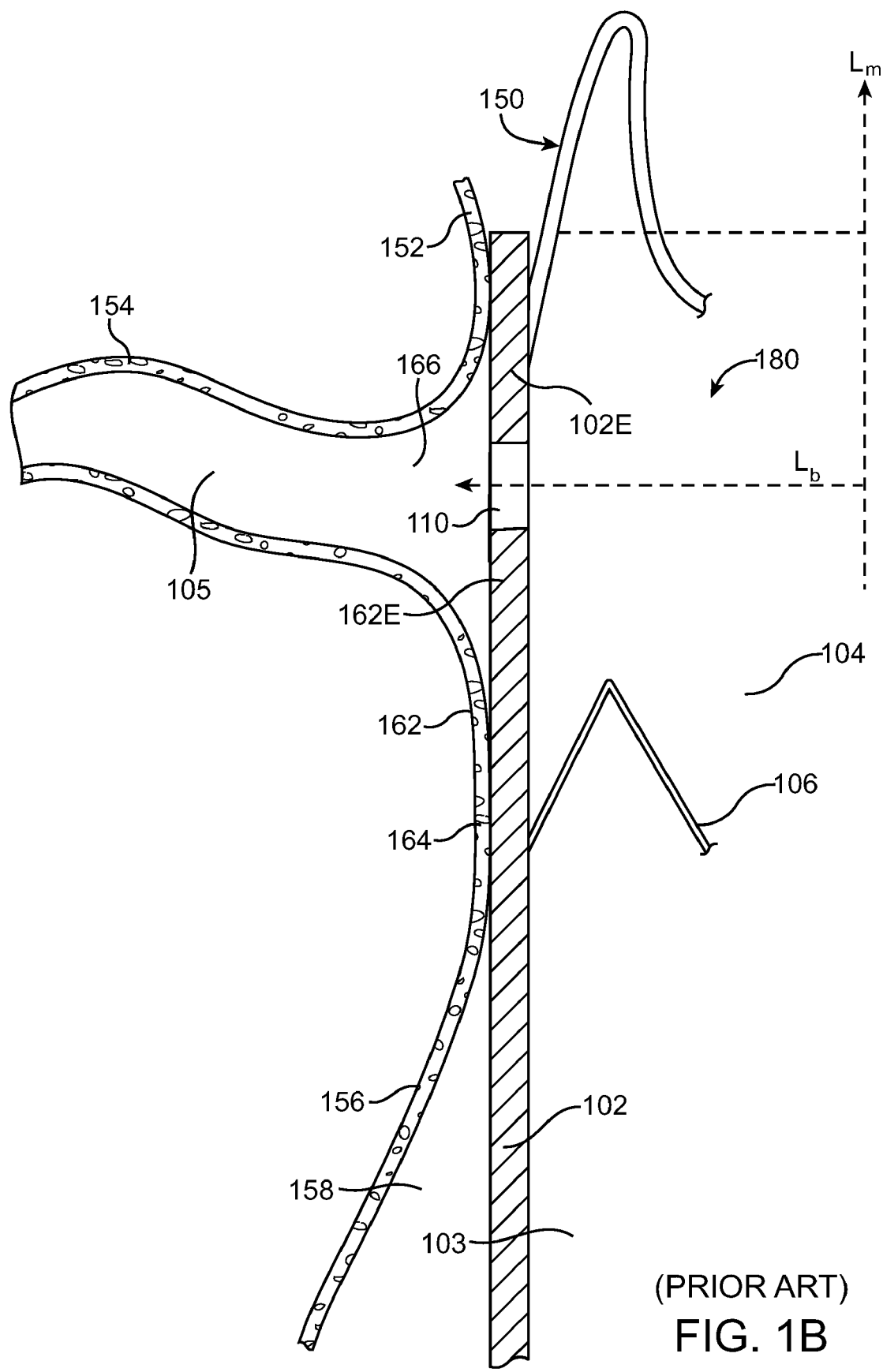
FIG. 1B shows a close-up, cross-section view at a branch of a vessel system similar to the one shown in FIG. 1A containing another example of a deployed prior art stent graft that further includes extended graft material beyond a branch point.

In one embodiment, at Insert/Advance Stent Graft Operation 604, a stent graft catheter (not shown) sheathing stent graft 200 in a compressed configuration is inserted into and advanced along vessel system 150, for example an artery system, through furcation 159 (FIG. 1A), for example an iliac artery, until stent graft 200 is in the general area of branch point 162 of vessel system 150. The insertion and advance of compressed stent grafts through intravascular procedures utilizing a guide wire (not shown) to direct the coursing of the stent graft catheter through vessel system 150 are well known to those of skill in the art and therefore are not described further.

In one embodiment, the advance and axial positioning of the stent graft catheter sheathing stent graft 200 through furcation 159 and main vessel 152 to the general location of branch point 162 is monitored through well-know vascular imaging and radiographic techniques, using one or more radiopaque markers (not shown) coupled to a known location on the stent graft catheter. Upon the stent graft catheter, or more particularly stent graft 200, reaching the general location of branch point 162, Operation 604 transfers to Position Stent Graft Axially Operation 608.

In Position Stent Graft Axially Operation 608, the axial position of stent graft 200 is adjusted along the direction of main body central axis $L_m$ so that branch graft 205 more closely aligns main axially with vessel ostium 166. After the adjustment, Operation 608 transfers to Stent Graft Accurately Positioned Axially Determination Operation 612.

In Stent Graft Accurately Positioned Axially Determination Operation 612, it is determined whether branch graft 205 is accurately positioned main axially with respect to vessel ostium 166. In Determination Operation 612, an axial misalignment distance "Z", (FIG. 7), between branch graft 205 and vessel ostium 166 is determined using radiographic or other visioning techniques.

If the outcome of Determination Operation 612 indicates that axial misalignment distance "Z" is greater than a distance that would provide effective deployment of branch graft 205 within branch vessel 154, Determination Operation 612 transfers back to Position Stent Graft Axially Operation 608 so that stent graft 200 may be repositioned within main vessel 203, main axially along main body central axis $L_m$, such that branch graft 154 more closely main axially aligns with vessel ostium 166.

Operations 608 and 612 makeup a Stent Graft Axial Repositioning Loop 616. Several iterations of Stent Graft Axial Repositioning Loop 616 may be needed to provide accurate axial positioning of stent graft 200 so that branch graft opening of the main body is main axially aligned with vessel ostium 166 within the flexible and articulable range of branch graft 205. Thus, Stent Graft Axial Repositioning Loop 616 is repeatedly performed until stent graft 200 is main axially positioned within main vessel 152 such that branch graft 205 may be effectively deployed within branch vessel 154 through vessel ostium 166.

Figure 8:
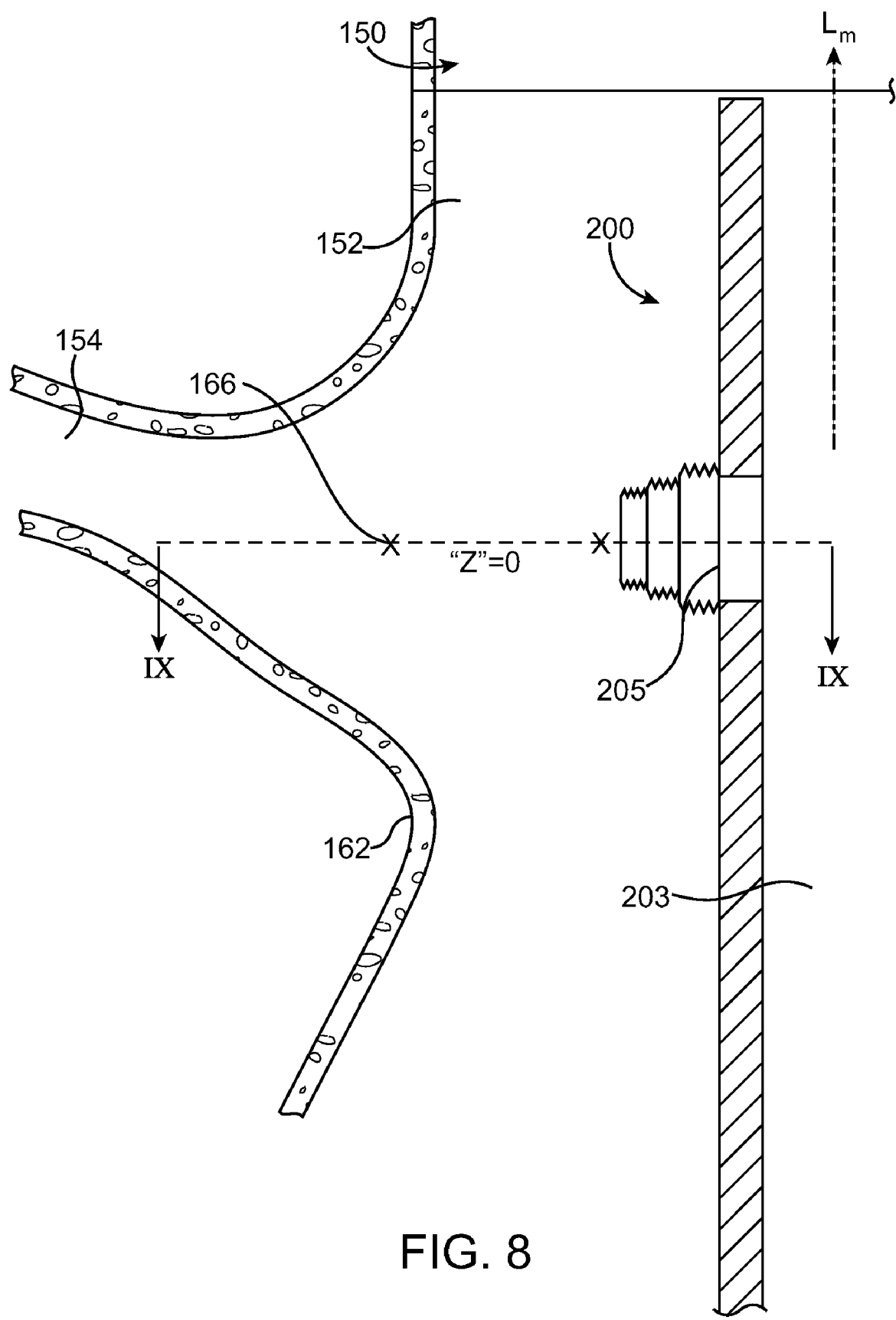
FIG. 8 shows a close-up partial cutaway view of vessel system containing an example of a stent graft in a compressed configuration and positioned along a main vessel such that a branch opening (aperture) and graft are substantially aligned with a vessel ostium.

At some point following Operation 608 within Loop 616, stent graft 200 is positioned as illustrated in FIG. 8. FIG. 8 shows a close-up partial cutaway view of vessel system 150 containing stent graft 200 in a compressed configuration and positioned along main vessel 152 such that branch graft 205 substantially aligns main axially with vessel ostium 166. When it is said that branch graft 205 substantially aligns main axially with vessel ostium 166 it is meant that main axially misalignment distance "Z" is within the flexibility and articulation range of branch graft 205.

Referring to FIGS. 6 and 8 together, as indicated above, in this final iteration of Loop 616, Operation 608 transfers to a final iteration of Determination Operation 612. In this final iteration of Stent Graft Accurately Positioned Axially Determination Operation 612, axial misalignment distance "Z" between branch graft 205 and vessel ostium 166 is determined to be sufficiently small that an effective deployment of branch graft 205 within branch vessel 154 may be accomplished if branch graft 205 is also properly aligned rotationally while branch graft 205 maintains this current main axial position relative to vessel ostium 166. In FIG. 8, substantial main axial alignment along the direction of main body central axis $L_m$ between branch graft 205 and vessel ostium 166 is represented by a nominal "zero" value for axial misalignment distance "Z".

When stent graft 200 is main axially position as just described and shown in FIG. 8, the angular relationship about main body central axis $L_m$ between vessel ostium 166 and branch graft 205 may also be determined. Hence, since Stent Graft Accurately Positioned Axially Determination Operation 612 is now true (YES), with stent graft 200 maintained main axially in its current position, Determination Operation 612 transfers to Position Stent Graft Rotationally Operation 618.

Figure 9:
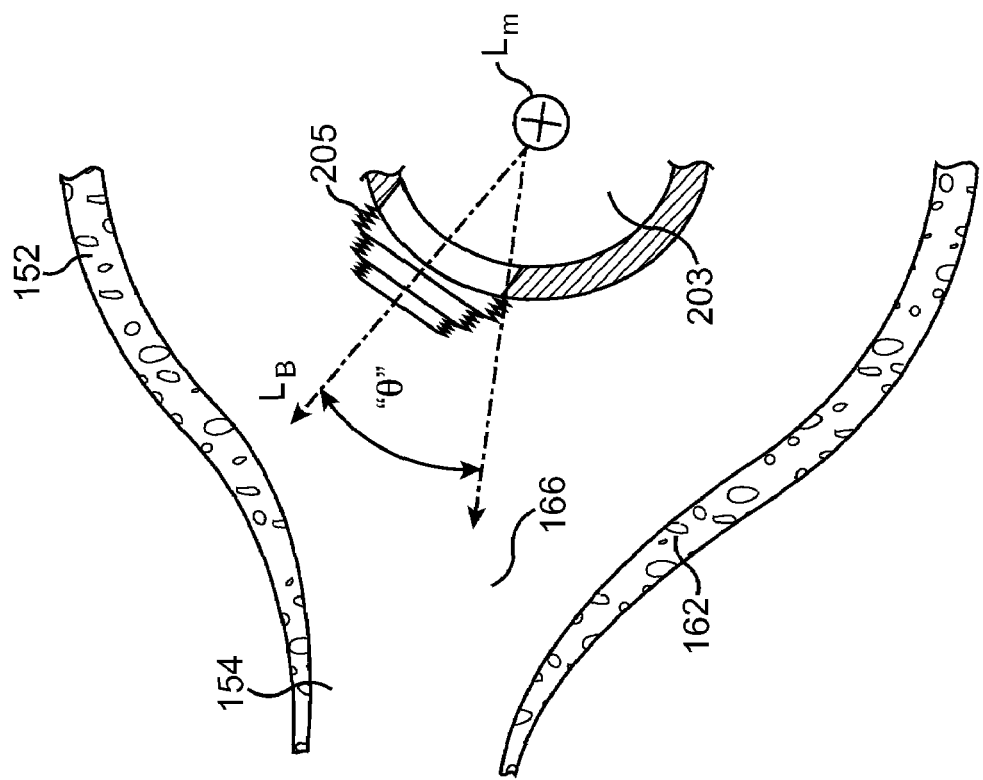
FIG. 9 shows a first cross sectional view taken along line IX-IX of FIG. 8 with the stent graft positioned in the main vessel such that the branch opening (aperture) and graft is rotationally misaligned with the vessel ostium.

FIG. 9 shows a first cross sectional view taken along line IX-IX of FIG. 8 of stent graft 200 positioned about main vessel 152 such that branch graft 154 is misaligned rotationally with vessel ostium 166. Referring to FIGS. 6 and 9 together, with stent graft 200 still in a compressed configuration to permit movement, in Position Stent Graft Rotationally Operation 618, the angular position of stent graft 200 is adjusted about the direction of main body central axis $L_m$ so that branch graft 205 more closely aligns rotationally with vessel ostium 166. After the adjustment, Operation 618 transfers to Stent Graft Accurately Positioned Rotationally Determination Operation 624.

As shown in FIG. 9, at Stent Graft Accurately Positioned Rotationally Determination Operation 624, a rotational misalignment angle "θ" is an angle between branch graft 205 and vessel ostium 166 about main body central axis $L_m$. Hence, a first pass through Determination Operation 624 determines that, as shown in FIG. 9, when viewed by radiographic or other visioning along main body central axis $L_m$ from above, branch graft 205 is rotationally misaligned clockwise with vessel ostium 166 by rotational misalignment angle "θ".

In this example, branch graft 205 is sufficiently rotationally misaligned with vessel ostium 166 such that deployment of branch graft 205 within branch vessel 154 is not possible.

Accordingly, upon completion of Determination Operation 624, Operation 624 transfers back to Position Stent Graft Rotationally Operation 618.

Operations 618 and 624 makeup a Stent Graft Rotational Repositioning Loop 628. Several iterations of Stent Graft Rotational Repositioning Loop 628 may be needed to provide accurate rotational alignment of branch graft 205 with vessel ostium 166.

At each Stent Graft Accurately Positioned Rotationally Determination Operation 624, rotational misalignment angle "θ" is re-determined. If, at the completion of Determination Operation 624, stent graft 200 must be repositioned rotationally about main vessel central axis $L_m$, Operations 618 and 624 are repeated.

Figure 10:
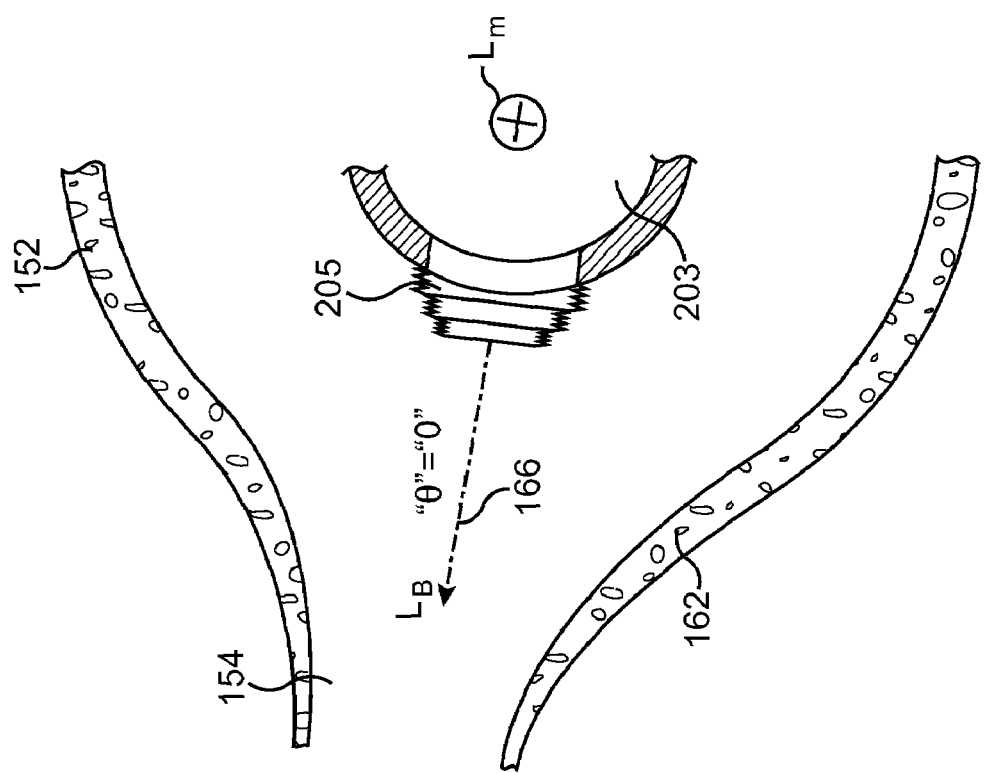
FIG. 10 shows a second cross sectional view taken along line IX-IX of FIG. 8 with the stent graft positioned about the main vessel such that the branch opening (aperture) and graft substantially aligns rotationally with the vessel ostium.

FIG. 10 shows a second cross sectional view taken along line IX-IX of FIG. 8 of stent graft 200 positioned about main vessel 152 such that branch graft 205 substantially aligns rotationally with vessel ostium 166. Referring to FIGS. 6 and 10 together, by completing sufficient iterations of Stent Graft Rotational Repositioning Loop 628, branch graft 205 is rotated counter-clockwise so that branch graft 205 is rotationally aligned with vessel ostium 166, as shown in FIG. 10. Substantial Rotational Alignment about the direction of main body central axis $L_m$ between branch graft 205 and vessel ostium 166 is represented by a nominal "zero"value for rotational misalignment angle "θ". Substantial rotational alignment occurs when branch graft 205 and vessel ostium 166 are relatively positioned rotationally, within the flexibility and articulation range of branch graft 205, such that branch graft 205 may be effectively deployed in branch vessel 154 through vessel ostium 166. Hence, at this point Determination Operation 624 is true (YES) for the example of FIG. 10 and Determination Operation 624 transfers to Expand Main lumen Radially Operation 626.

Figure 11:
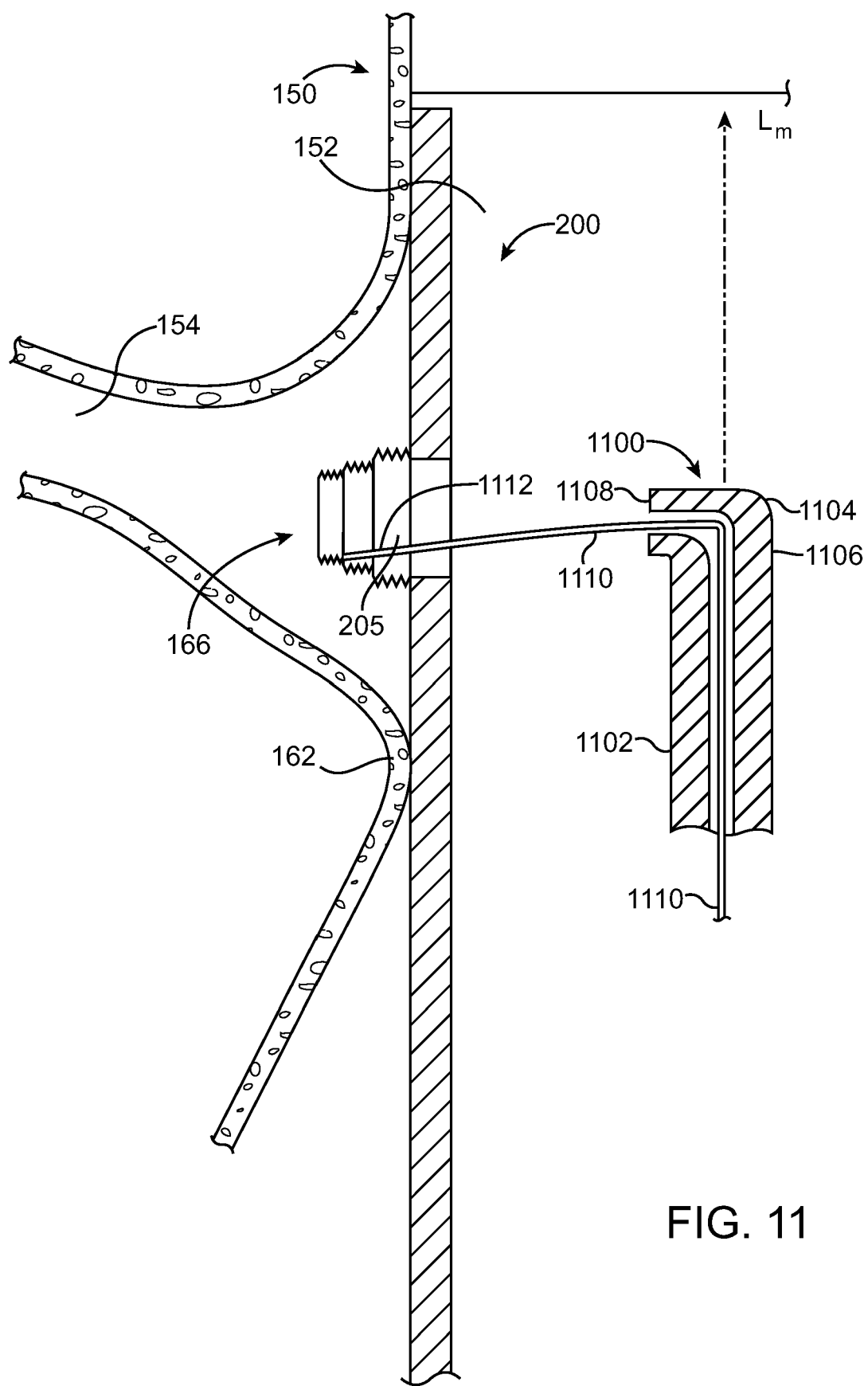
FIG. 11 shows a close-up partial cutaway view the vessel containing the stent graft positioned as in FIG. 10 but with the main body in an expanded configuration.
Figure 12:
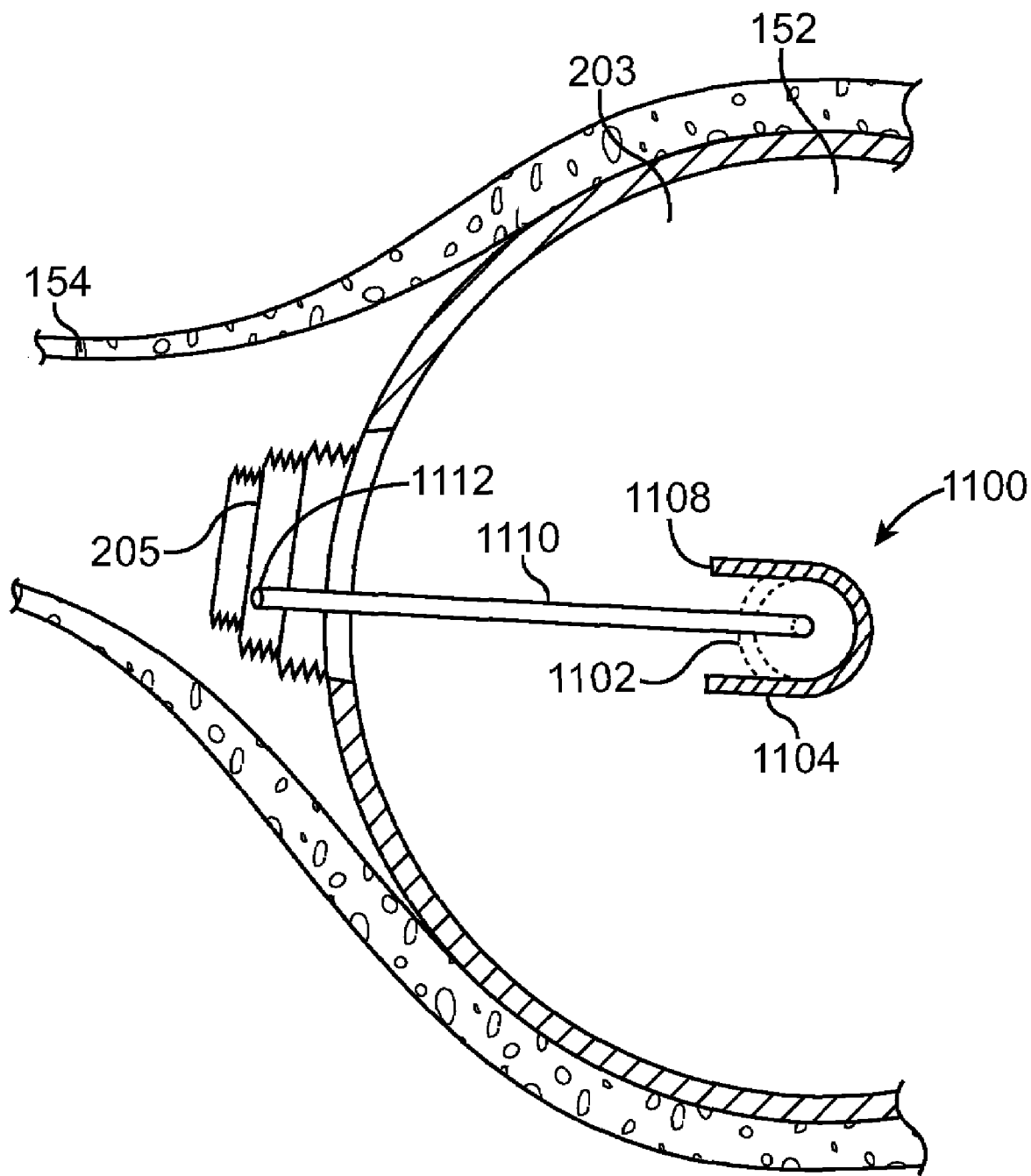
FIG. 12 shows the stent graft positioned and expanded as in FIG. 11 and further shows a branch graft expansion catheter used to branch axially (laterally) extend the branch graft.

FIG. 11 shows a close-up partial cutaway view the vessel containing the stent graft positioned as in FIG. 10 but with the main graft body in an expanded configuration. FIG. 12 shows stent graft 200 positioned and expanded as shown in FIG. 11 and further shows a branch graft expansion catheter 1100 used to axially expand branch graft 205. Referring to FIGS. 6, 11 and 12 together, at Expand Main lumen Radially Operation 626 (FIG. 6) following Determination Operation 624, a stent graft catheter sheath (not shown) constraining stent graft 200 in a compressed configuration (FIGS. 9 and 10) is drawn back from or removed from the stent graft catheter (not shown) used to position stent graft 200 as described above. Stent graft 200, or more particularly main body 203, radially expands outward from main body central axis $L_m$ to contact the interior wall of main vessel 152 (FIGS. 11 and 12). In one example, main body 203 is self expanding and, in another example, main body 203 is expanded by means of an expansion balloon (not shown) inserted into main vessel 152 and advanced to main body 203 in a manner well known to those of skill in the art.

With main body 203 in an aligned and expanded configuration, in one example, Operation 626 (FIG. 6), transfers to Insert/Advance Branch graft Expansion Catheter Operation 630. In this example, a flexible branch graft expansion catheter 1100 is used to axially expand branch graft 205 (FIGS. 11 and 12) into branch vessel 154. Branch graft expansion catheter 1100 includes a hollow main piece 1102 of generally straight tubular shape, and a turning piece 1104 formed as a hollow tubular shaped bend of approximately 90° coupled at a turner piece first end 1106 (FIG. 11) to a distal end of main piece 1102. A flexible deployment wire 1110, is slidibly movable within branch graft expansion catheter 1100.

At Insert/Advance Branch graft Expansion Catheter Operation 630, branch graft expansion catheter 1100 is inserted into main vessel 152 and advanced to branch graft 205 in a manner analogous to that described with respect to Insert/Advance Stent Graft Operation 604 above and is therefore not repeated here with respect to Operation 630.

Next, after completion of Insert/Advance Branch graft Expansion Catheter Operation 630, to substantially align turning piece second end 1108 with branch graft 205, Position Branch graft Expansion Catheter Axially Operation 634 followed by Branch graft Expansion Catheter Accurately Positioned Axially Determination Operation 636, together making up Branch graft Expansion Catheter Axial Repositioning Loop 638, is iterated in the manner described above with reference to Stent Graft Axial Repositioning Loop 616 and so are not repeated here.

Next, to rotationally substantially align turning piece second end 1108 with branch graft 205, at Position Branch Lumen Expansion Catheter Rotationally Operation 640 followed by Branch graft Expansion Catheter Accurately Positioned Rotationally Determination Operation 642, together making up Branch graft Expansion Catheter Rotational Repositioning Loop 644, is iterated as also described above with reference to stent graft 200.

Thus, at some point following a last iteration of Determination Operation 642 turning piece second end 1108 of branch graft expansion catheter 1100 substantially aligns main axially and rotationally with branch graft 205 as shown in FIGS. 11 and 12. When it is said that turning piece second end 1108 substantially aligns main axially and rotationally with branch graft 205, it is meant that branch graft expansion catheter 1100 may be used to effectively expand branch graft 205 along branch graft central axis $L_b$.

Next, after turning piece second end 1108 is positioned as just described, Operation 642 transfers to Expand Branch graft Axially Operation 646 where deployment wire 1110 is slidibly advanced within branch graft expansion catheter 1100, flexibly bending toward compressed branch graft 205 when advanced within turning piece 1104. With further advance of deployment wire 1110 beyond turning piece second end 1108, a deployment wire distal end 1112 of deployment wire 1110 contacts and branch axially expands branch graft 205 along branch graft central axis $L_b$.

As described, by Method 600, branch graft 205 is previously positioned both main axially (FIG. 12) and rotationally (FIG. 11) adjacent vessel ostium 166 leading into branch vessel 154. Thus, at Expand Branch graft Axially Operation 646, branch graft 205 deploys within branch vessel 154, as shown in FIGS. 2 and 3, when it is axially expanded along branch graft central axis $L_b$ by operation of deployment wire distal end 1112.

After branch graft 205 is axially expanded and deployed within branch vessel 154, deployment wire 1110 is retracted from its deployment configuration and is returned within branch graft expansion catheter 1100 by slidibly moving deployment wire 1110 in a direction opposite of that used to expand and deploy branch graft 205. After, deployment wire 1110 is retracted, branch graft expansion catheter 1100 is withdrawn from vessel system 150, which completes Expand Branch graft Axially Operation 646, thereby ending Method 600 at End Operation 648. At this point stent graft 200 is fully deployed as shown in FIGS. 2 and 3.

In examples of stent graft 200 that include branch grafts 205 that are self expanding, branch graft 205 is branch axially self expanded and deployed within branch vessel 154 without use of branch graft expansion catheter 1100. Accordingly, Operation 630 through 644 are not implemented and Expand Main body Radially Operation 626 is followed directly by Expand Branch graft Axially Operation 646 where branch graft 205 self expands.

Thus, stent grafts include branch grafts that are flexible and articulable. Method 600 provides a process that, prior to deployment, easily accommodates compression of the entire stent graft and easily accommodates a relatively large degree of main axial and angular misalignment between branch grafts and the branch vessel into which the branch grafts are deployed. Further, after the operations of Method 600 are successfully completed, the flexible and articulable branch grafts easily conform, without kinking or collapsing, to the tortuous nature of the respective branch vessels into which they are deployed.

The sequence of operations and the operations in Method 600 are illustrative only and are not intended to limit either the sequence of operations or the specific operations. For example, the axial and radial positioning operations could be done together rather than as separate operational loops.

In another example Method 600 may be utilized to place a bifurcated stent graft including a separate fenestrated main body, having a branch opening (aperture) in the main graft material making up the main body, and a separate branch graft. By Method 600 the fenestrated main body is longitudinally aligned with a vessel ostium leading to the branch graft and deployed in the main vessel of the vessel system. The separate branch graft is next aligned with the branch opening (aperture) of the main body and branch axially expanded, by Method 600, through the main body branch opening (aperture) through the vessel ostium and into the branch vessel. The branch graft is coupled to the main body at the main body branch opening (aperture) by techniques well know to those of skill in the art.

In general, those of skill in the art can alter the sequence and operations so long as the sequence of operations positions the branch graft substantially adjacent to the vessel ostium of a branch vessel into which the flexible and articulable branch graft is to be deployed.

Figure 13:
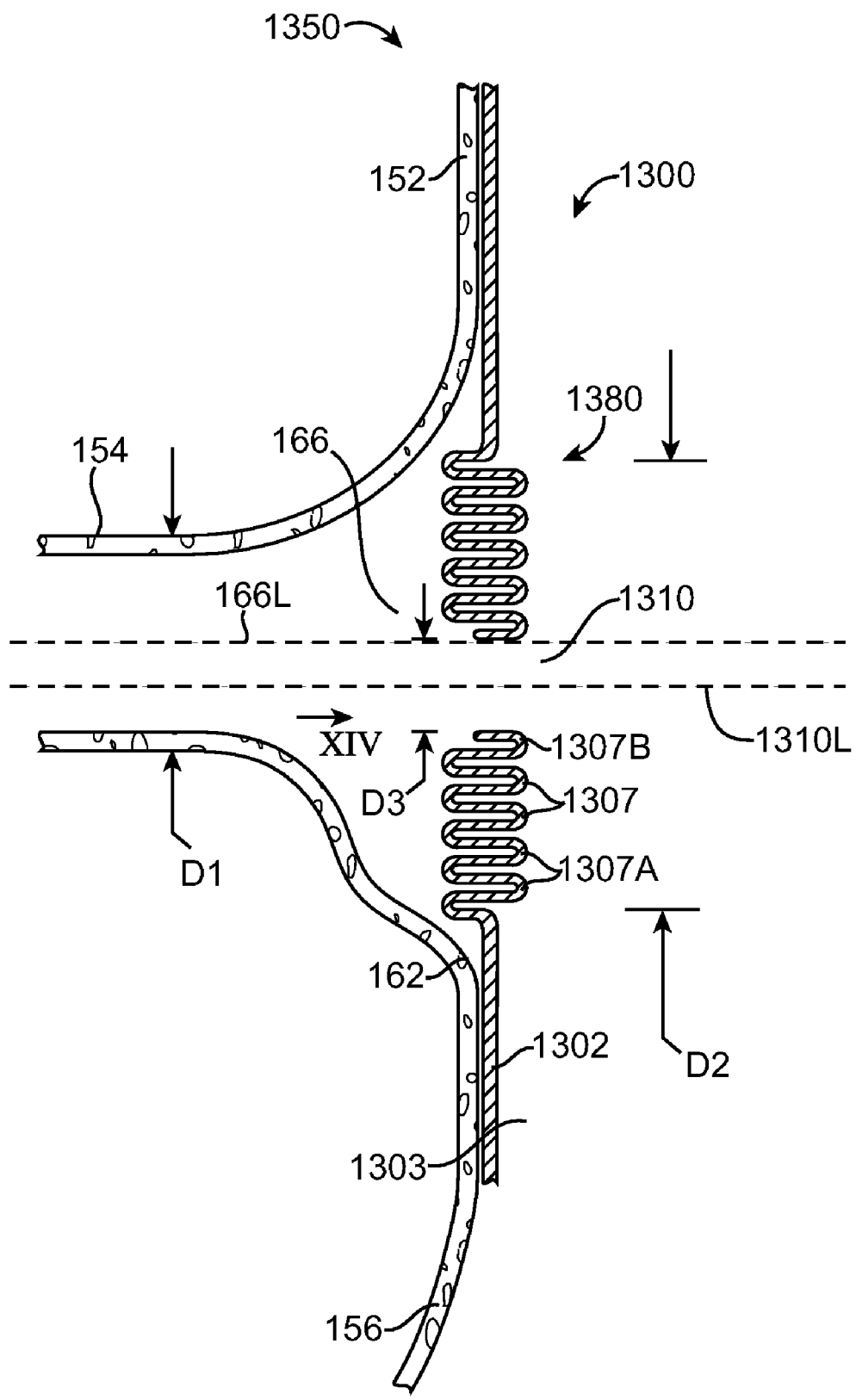
FIG. 13 shows a close-up partial cutaway view of a vessel system containing a stent graft that includes an example of a fenestration assembly.
Figure 14:
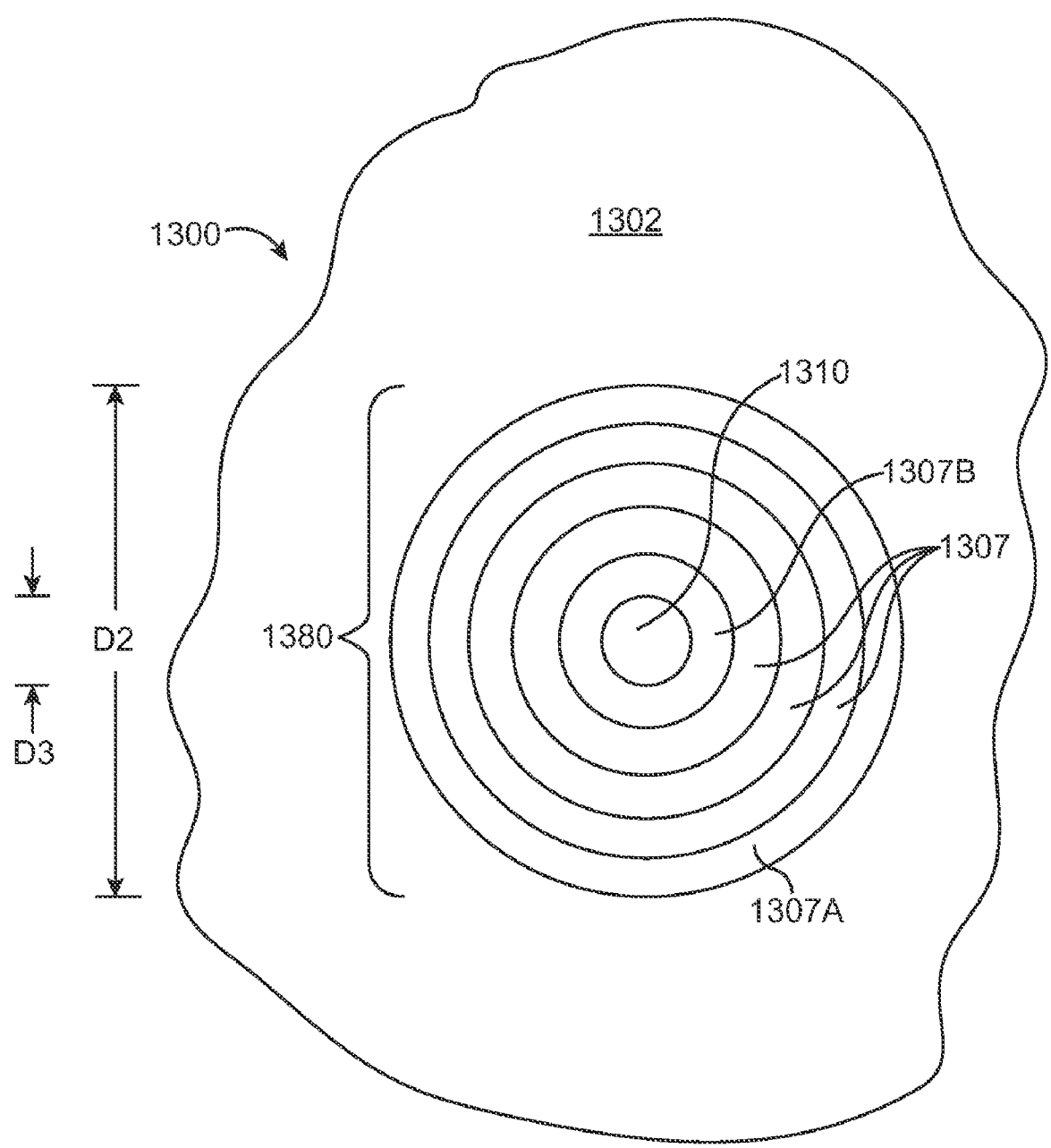
FIG. 14 shows a side plan view of a portion of the stent graft of FIG. 13 taken along the line XIV.

FIG. 13 shows a close-up partial cutaway view of a vessel system 1350 containing a stent graft 1300 that includes an example of fenestration assembly 1380 in accordance with one embodiment of the present invention. FIG. 14 shows a side plan view of a portion of stent graft 1300 of FIG. 13 taken along the line XIV. For clarity of presentation, in FIGS. 13 and 14, the previously described stent reinforcing structures and bare spring elements are not shown, although it should be understood that stent graft 1300 may include some or all of these structures in certain examples. Generally, stent graft 1300 may include self expanding or balloon expandable stents as is well known to those of skill in the art.

Referring to FIGS. 13 and 14 together, a main graft material 1302, sometimes called a wall, is configured in a tubular shape defining a main body 1303 spanning across an aneurysm 156 affecting a main vessel 152, for example, an artery. Vessel system 1350 includes one or more branch vessels(e.g., 154), for example, renal arteries, emanating from main vessel 152 at branch point (e.g., 162). Main vessel 152 includes a vessel ostium 166 in main vessel 152 leading into branch vessel 154, thereby placing branch vessel 154 in fluid communication with main vessel 152.

Positioned for deployment in branch vessel 154, is a fenestration assembly 1380, sometimes called a corrugated hole. Fenestration assembly 1380 includes at least one series of connected pleats 1307 formed from biocompatible material, e.g., graft material. Fenestration assembly 1380 defines an branch opening (aperture) 1310 in main body 1303. Fenestration assembly 1380 is coupled to or integral with main graft material 1302 such that fenestration assembly 1380 is in fluid communication with main body 1303.

As described more fully below with reference to FIG. 15, fenestration assembly 1380 formed of connected pleats 1307 makes fenestration assembly 1380 flexible and articulable in the manner of a bellows. Said by way of simile, fenestration assembly 1380, formed of connected pleats 1307, provides fenestration assembly 1380 with the flexible and articulable characteristics of an "elephant trunk". The particular properties of fenestration assembly 1380 allow stent graft 1300 to accommodate a relatively large degree of misalignment between fenestration assembly 1380 and vessel ostium 166 prior to deployment. Additionally, flexible and articulable fenestration assembly 1380 easily conforms, without kinking or collapsing, to the tortuous nature of branch vessel 154 after deployment.

Connected pleats 1307, sometimes called corrugations, are formed as ring structures, one within another, of decreasing diameter. To illustrate, an outer pleat 1307A of connected pleats 1307 is attached, i.e., connected to or integral with, main graft material 1302. Outer pleat 1307A defines a first branch opening (aperture)(ring) in main graft material 1302 of stent graft 1300.

Outer pleat 1307A has the greatest diameter D2 of pleats 1307, i.e., fenestration assembly 1380 has a diameter D2. Conversely, an inner pleat 1307B of connected pleats 1307 defines branch opening (aperture)(ring) 1310. Inner pleat 1307B, sometimes called a second ring, defines a smaller branch opening (aperture), e.g., branch opening (aperture) 1310, within outer pleat 1307A.

Inner pleat 1307B has the smallest diameter D3 of pleats 1307. The other pleats between outer pleat 1307A and inner pleat 1307B have a decreasing diameter from outer pleat 1307A to inner pleat 1307B. Further, in one example, pleats 1307 are one within another, e.g., are concentric ring structures. For example, pleats 1307 lie along the cylindrical surface defined by main graft material 1302. More specifically, outer pleat 1307A and inner pleat 1307B are concentric in one example.

In one example, pleats 1307 are formed of a graft material extending between outer pleat 1307A and inner pleat 1307B. The graft material enables movement, e.g., orbital, eccentric, and/or angular movement, of inner pleat 1307B with respect to outer pleat 1307A. Stated another way, the graft material is concentrically corrugated into pleats 1307, allowing flexible positioning of inner pleat 1307B within outer pleat 1307A. Illustratively, the graft material includes biocompatible flexible material allowing flexible positioning of inner pleat 1307B within outer pleat 1307A.

As shown in FIG. 13, vessel ostium 166 of branch vessel 154 has a diameter D1. As set forth above, fenestration assembly 1380 has a diameter D2. In one example, diameter D2 of fenestration assembly 1380 is greater than diameter D1 of branch vessel 154 accommodating a greater amount of acceptable misalignment between fenestration assembly 1380 and branch vessel 154. More particularly, as long as vessel ostium 166 of branch vessel 154 is aligned with the area defined by fenestration assembly 1380, more particularly, defined by outer pleat 1307A, fenestration assembly 1380 is sufficiently aligned with vessel ostium 166 of branch vessel 154 for proper deployment of fenestration assembly 1380 within branch vessel 154 as shown in FIG. 15.

To illustrate, branch opening (aperture) 1310 defined by inner pleat 1307B has a branch axis 1310L. Vessel ostium 166 of branch vessel 154 has a branch axis 166L. Branch axis 166L of vessel ostium 166 is misaligned with branch axis 1310L of branch opening (aperture) 1310, branch axis 1310L of branch opening (aperture) 1310 being below branch axis 166L of vessel ostium 166 as shown in FIG. 13. However, as set forth above, this misalignment of branch axis 1310L of branch opening (aperture) 1310 with branch axis 166L of vessel ostium 166 is acceptable since vessel ostium 166 of branch vessel 154 is aligned with the area defined by outer pleat 1307A.

Figure 15:
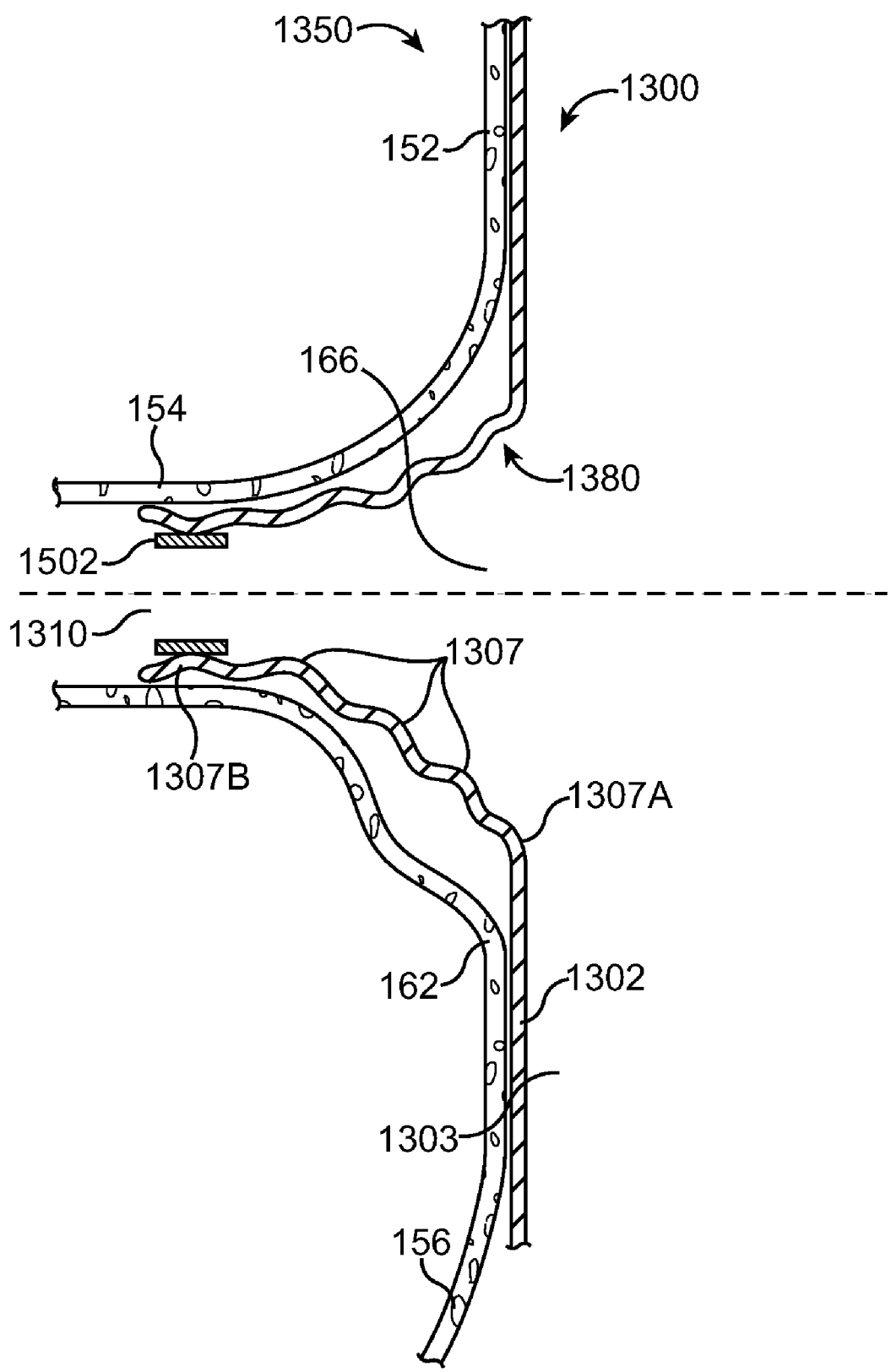
FIG. 15 shows a close-up partial cutaway view of the vessel system containing the stent graft of FIG. 13 after securement of the fenestration assembly in a branch vessel.

FIG. 15 shows a close-up partial cutaway view of vessel system 1350 containing stent graft 1300 of FIG. 13 after securement of fenestration assembly 1380 in branch vessel 154. As shown in FIG. 15, the lower portion of pleats 1307 is stretch apart further than the upper portion of pleats 1307 allowing fenestration assembly 1380 to be inserted within branch vessel 154. Fenestration assembly 1380 is inserted within branch vessel 154 in a manner similar to that discussed above, and so is not repeated. In accordance with this example, a securement member 1502, e.g., a self-expanding stent, anchors fenestration assembly 1380, e.g., inner pleat 1307B, within branch vessel 154.

Figure 16:
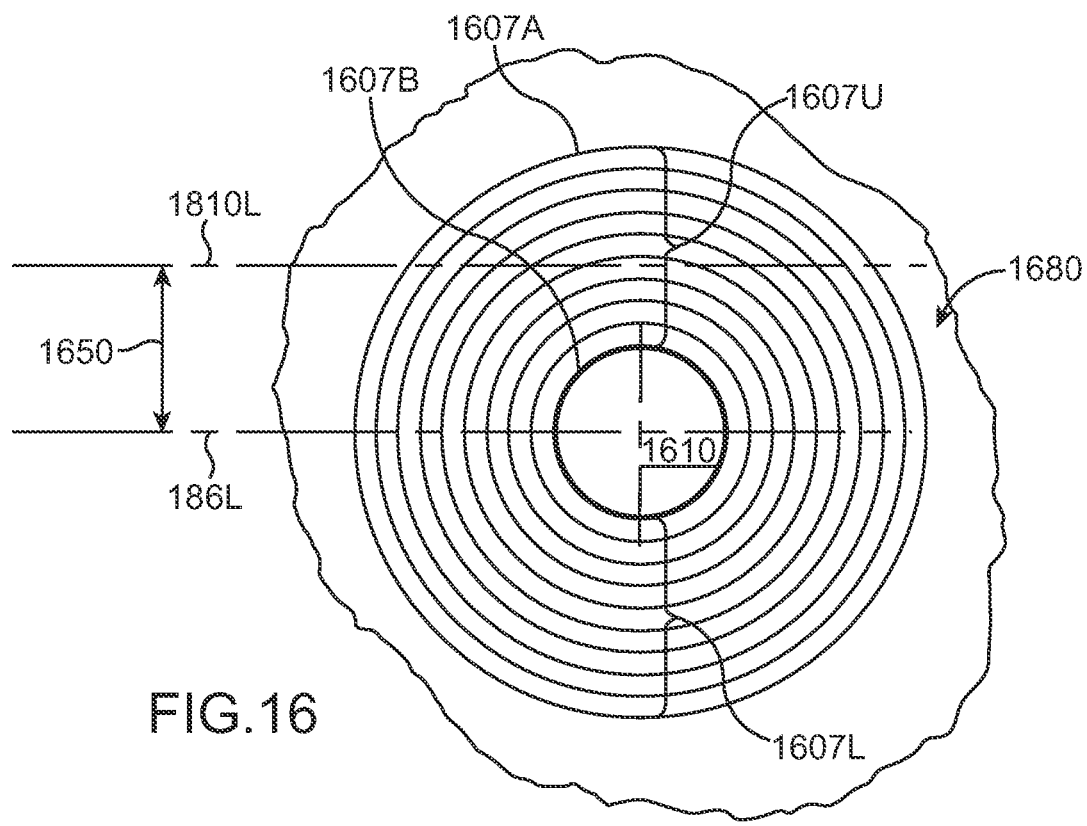
FIG. 16 show a close-up plan view of a relaxed configuration of a main body side opening whose position is variable within flexibility limits of the surrounding corrugations or pleats laterally and vertically in the confines of the cylindrical shape that constitutes the wall structure of the main body.
Figure 19:
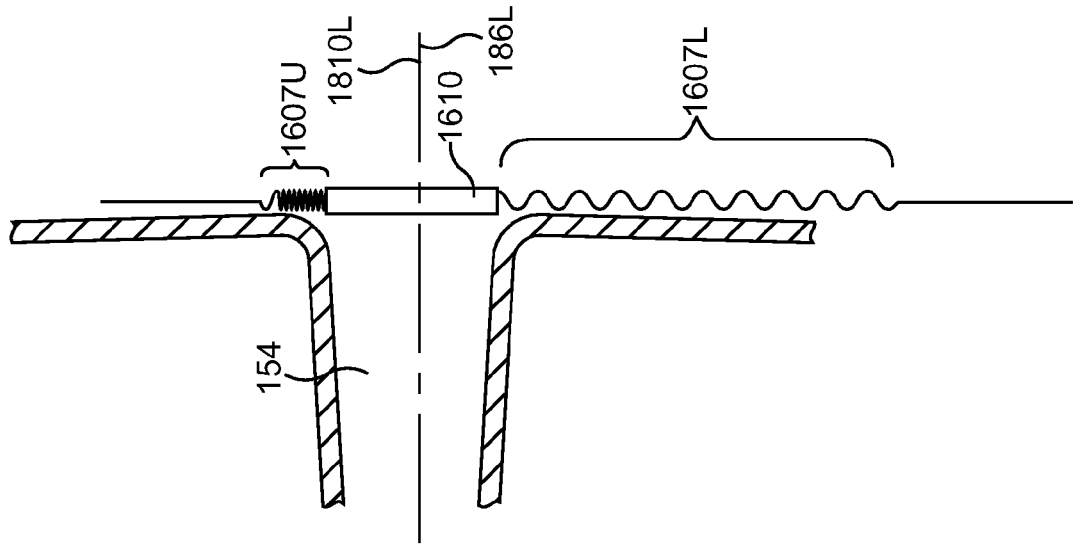
FIG. 19 is a close up cross sectional view of the vertically displaced configuration of the main body side opening of FIG. 17, where the centerline of the side opening in this displaced configuration is positioned substantially aligned with the center line of the branch vessel so that blood flow from the main vessel to the branch vessel is substantially clear and is not blocked by the close adjacent wall of the main vessel.
Figure 18:
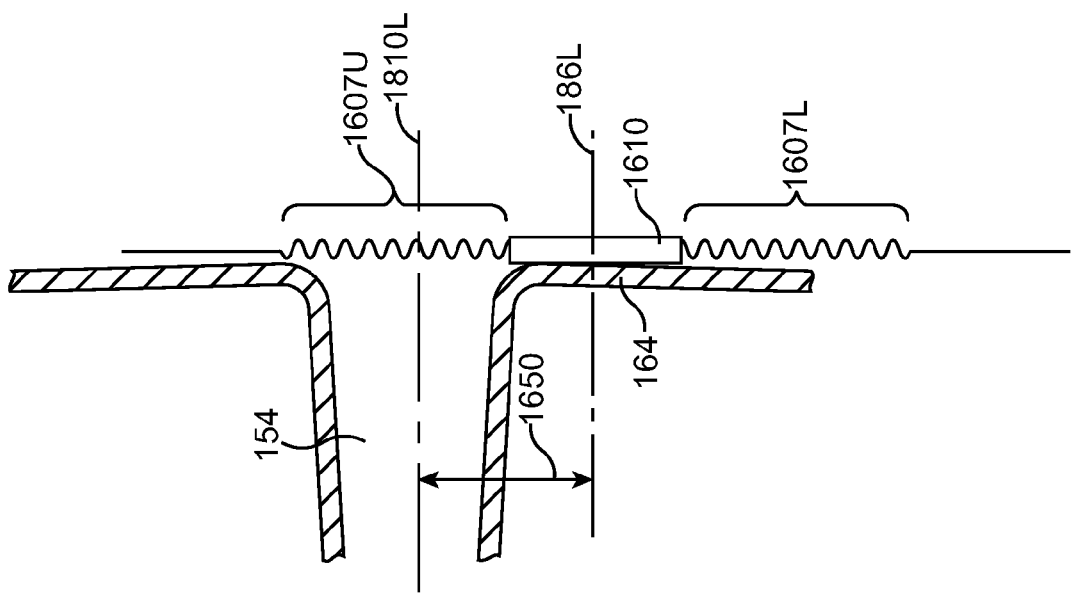
FIG. 18 is a close up cross sectional view of the relaxed configuration of the main body side opening of FIG. 16, where the centerline of the side opening in its relaxed configuration is positioned below and substantially blocked by the close adjacent wall of the main vessel.

FIG. 16 show a close-up plan view of a relaxed configuration of a fenestration assembly 1680: a main body side opening (small ring) 1610 having a surrounding pleat (or ring) 1607B whose position is variable within flexibility limits of the surrounding corrugations or pleats, e.g., 1607, laterally and vertically (within the confine of an outer pleat (or ring) 1607A in the confines of the tubular cylindrical shape that constitutes the wall structure of the main body near the location of branch vessels emanating from the main vessel as shown in FIGS. 18 and 19. FIG. 16 pictures elements similar to those discussed for FIG. 14 above. In this relaxed configuration, the upper portion of the fenestration assembly have a pleats spanned dimension 1607U that is approximately equal to the lower portion of the fenestration assembly pleats spanned dimension 1607L.

Figure 17:
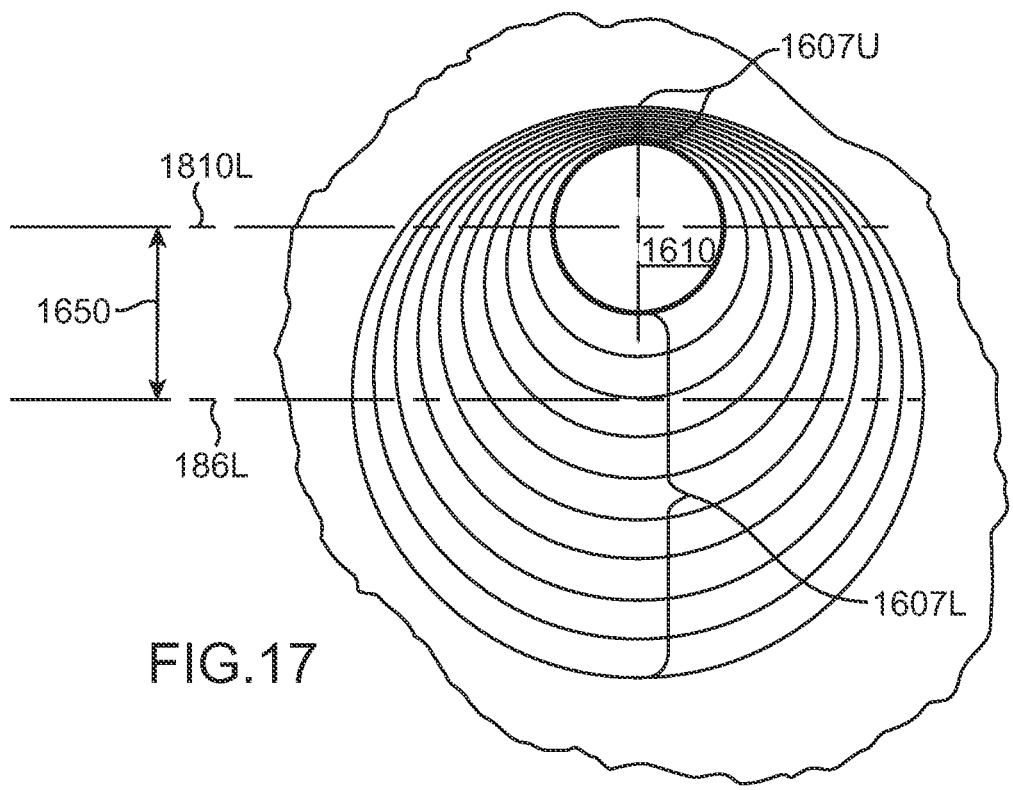
FIG. 17 show a close-up plan view of a highly displaced configuration of a main body side opening where the opening position has been moved to a near top extreme of vertical flexibility limits of the surrounding corrugations or pleats that constitute the sidewall of the main body.

FIG. 17 show a close-up plan view of the fenestration assembly of FIG. 16 with a highly displaced configuration of the main body side opening 1610 whose position has been moved to a near top extreme of vertical flexibility limits of the surrounding corrugations or pleats 1607 that constitute the fenestration assembly in the sidewall of the main body. The side opening 1610 has been displaced upwards an offset distance 1650 from its relaxed position as shown in FIG. 16. In this configuration the upper portion of the fenestration assembly has pleats spanned dimension 1607U which has substantially diminished from that shown in FIG. 16, while the lower portion of the fenestration assembly pleats spanned dimension 1607L is substantially greater than from that shown in FIG. 16. The change in each of the upper and lower pleats spanned dimensions 1607U, 1607L is substantially equal to the center offset distance 1650.

FIG. 18 is a close up cross sectional view of the relaxed configuration of the main body side opening 1610 of FIG. 16, where the centerline of the fenestration assembly side opening in its relaxed configuration is positioned below and substantially blocked by the close adjacent wall (neck) 164 of the main vessel. As can be seen in FIGS. 16 and 18 the stent graft is shown deployed where a central axis 186L of the branch opening 1610 has been implanted an offset distance 1650 below the center line 1810L of the branch vessel 154.

FIG. 19 is a close up cross sectional view of the vertically displaced configuration of the main body side opening shown in FIG. 17, where the centerline 186L of the side opening 1610 in this displaced configuration is positioned substantially aligned with the center line 1810L of the branch vessel 154 so that blood flow from the main vessel to the branch vessel is substantially clear and is not blocked by the close adjacent wall (neck) 164 of the main vessel. A guidewire or catheter (not shown) used to guide and/or deploy a branch graft through the side branch opening is used to provide the vertical force needed to achieve the vertical offset distance 1650 shown here. In the configurations shown in FIG. 16-19, the ostium of the branch vessel is located approximately at the diameter of the main body at the location of the branch vessel. In this configuration there is no opportunity for portions of a fenestration assembly to extend laterally outward because of the closely adjacent main vessel wall (neck). So in this configuration as in others where a lateral extension of the corrugations are not desired, a branch graft assembly, e.g., those shown in the Wisselink U.S. Pat. Nos. 5,984,955 and 6,428,565. incorporated herein by reference, can be used to attach to the branch opening 1610 of the present fenestration assembly.

While particular embodiments have been described, those skilled in the art will understand that these embodiments are exemplary of the spirit and scope of the invention.

What is claimed is:

1. A stent graft including a wall having at least one fenestration assembly, wherein the wall defines a cylindrical surface, the fenestration assembly including:
    rings comprising a first ring and a second ring, the rings being one within another, the rings lying upon the cylindrical surface, the first ring defining a first aperture in the wall of the stent graft and the second ring defining a smaller aperture within the first ring, wherein the first ring is attached to the wall; and
    flexible and articulable graft material extending between the first ring and the second ring, whereby movement of the second ring with respect to the first ring is enabled, wherein the graft material extending between the first ring and the second ring is concentrically corrugated such that the second ring is within the first ring, and further wherein the first ring and the second ring are concentric.

2. A stent graft as in claim 1 wherein the graft material extending between the first ring and the second ring enables orbital or eccentric movement of the second ring with respect to the first ring.

3. A stent graft as in claim 1 wherein the graft material extending between the first ring and the second ring enables an angular movement of the second ring with respect to the first ring.

4. A stent graft as in claim 1 wherein the graft material extending between the first ring and the second ring comprises a biocompatible flexible material, whereby to allow flexible positioning of the second ring within the first ring.

5. A stent graft as in claim 1 wherein the rings are of decreasing diameter.

6. A stent graft as in claim 1 wherein the rings diminish in diameter from the first ring to the second ring.

7. A stent graft as in claim 1 wherein the rings are concentric.

8. A stent graft as in claim 1 further comprising a branch graft assembly coupled to the fenestration assembly.

* * * * *